US006677378B2

(12) United States Patent
Howard, Jr. et al.

(10) Patent No.: US 6,677,378 B2
(45) Date of Patent: Jan. 13, 2004

(54) MONOAMINE REUPTAKE INHIBITORS FOR TREATMENT OF CNS DISORDERS

(75) Inventors: Harry R. Howard, Jr., Bristol, CT (US); Christopher J. Schmidt, Old Lyme, CT (US); Thomas F. Seeger, Mystic, CT (US); Mark L. Elliott, Canterbury, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/845,992

(22) Filed: Apr. 30, 2001

(65) Prior Publication Data

US 2002/0143003 A1 Oct. 3, 2002

Related U.S. Application Data

(63) Continuation-in-part of application No. 09/529,207, filed as application No. PCT/IB00/00108 on Feb. 2, 2000, now abandoned.
(60) Provisional application No. 60/121,313, filed on Feb. 23, 1999.

(51) Int. Cl.$^7$ ............................................. A61K 31/137
(52) U.S. Cl. ........................................ 514/649; 564/336
(58) Field of Search ................. 514/649, 650, 514/471; 564/336; 549/491; 546/216

(56) References Cited

U.S. PATENT DOCUMENTS 1,161,529 A  11/1915  Ringer
6,410,736 B1 * 6/2002  Howard, Jr. et al. ........ 546/216

FOREIGN PATENT DOCUMENTS

EP  0516234  5/1992
EP  0807621  5/1997
RU  2139277  2/1997
SU  1208765  6/1984

OTHER PUBLICATIONS

Database CSChem, Chemical Sources International, Inc. Retrieved from STN Database Accession No. 11250, XP002135477. 2–Aminomethyl–3–Chlorodipfenylether.

* cited by examiner

*Primary Examiner*—Joseph K. McKane
*Assistant Examiner*—Kamal Saeed
(74) *Attorney, Agent, or Firm*—P. C. Richardson; P. H. Ginsburg; A. D. Joran

(57) ABSTRACT

The present invention relates to compounds of the formula

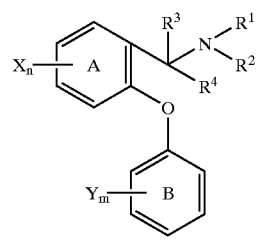

I wherein $R^1$ through $R^4$, X, Y, m and n are defined as in the specification. Such compounds are useful exhibit activity as serotonin, norepinephrine and dopamine reuptake inhibitors, and their pharmaceutically acceptable salts, and their use in the treatment of central nervous system and other disorders.

8 Claims, No Drawings

MONOAMINE REUPTAKE INHIBITORS FOR TREATMENT OF CNS DISORDERS

The present application is a continuation-in-part of U.S. Ser. No. 09/529,207, which was filed on Apr. 7, 2000 now abandoned as the U.S. national phase of World Patent Application PCT/IB00/00108, which was filed in the International Bureau of the PCT on Feb. 2, 2000. The present application claims priority from both the foregoing U.S. and World patent applications, as well as from U.S. Provisional Application Serial No. 60/121,313 filed Feb. 23, 1999.

BACKGROUND OF THE INVENTION

Serotonin Selective Reuptake Inhibitors (SSRIs) currently provide efficacy in the treatment of major depressive disorder (MDD) and are generally perceived by psychiatrists and primary care physicians as effective, well-tolerated and easily administered. However, they are associated with undesirable features, such as high incidence of sexual dysfunction, delayed onset of action and a level on non-responsiveness estimated to be as high as 30% (see M. J. Gitlin, Journal of Clinical Psychiatry, 1994, 55, 406–413 and R. T. Segraves, Journal of Clinical Psychiatry, 1992, 10(2), 4–10). Preclinical and clinical evidence has indicated that the sexual dysfunction associated with SSRI therapy can be reduced through the use of dopamine reuptake inhibitors (DRIs), such as bupropion (see A. K. Ashton, Journal of Clinical Psychiatry, 1998, 59(3), 112–115). Furthermore, the combination of SRI and DRI may hasten the onset of action as well as offering relief to refractory patients, possibly through a synergistic mechanism (see R. D. Marshall et al, Journal of Psychopharmacology, 1995, 9(3), 284–286).

This invention relates to novel biaryl ether derivatives that exhibit activity as monoamine (e.g., dopamine, serotonin) reuptake inhibitors, to pharmaceutical compositions containing such compounds and to methods of using such compounds to treat central nervous system (CNS) and other disorders.

U.S. Pat. No. 4,018,830, published on Apr. 19, 1997, refers to phenylthioaralkylamines and 2-phenylthiobenzylamines which are active as antiarrhythmics.

PCT publication 97/17325, published on May 15, 1997, refers to derivatives of N,N-dimethyl-2-(arylthio)benzylamine which selectively influence serotonin transport in the central nervous system and are useful as antidepressants.

U.S. Pat. No. 5,190,965, published on Mar. 2, 1993, and U.S. Pat. No. 5,430,063, issued Jul. 4, 1995, refer to phenoxyphenyl derivatives which have utility in the treatment of depression.

U.S. Pat. No. 4,161,529, published on Jul. 17, 1979, refers to pyrrolidine derivative which possess anticholesteremic and hypolipemic activity.

SUMMARY OF THE INVENTION

The present invention relates to compounds of the formula

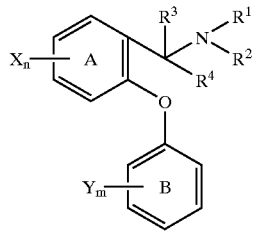

wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$alkyl optionally substituted with from one to three fluorine atoms, or $R^3$ and $R^4$ together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from hydrogen, halo (i.e., chloro, fluoro, bromo or iodo), $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-$[(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Y is selected, independently, from hydrogen, $(C_1-C_6)$alkyl and halo;

with the proviso that: (a) no more than one of $NR^1R^2$, $CR^3R^4$ and $R^2NCR^3$ can form a ring; and (b) at least one X must be other than hydrogen when (i) $R^3$ and $R^4$ are both hydrogen, (ii) $R^1$ and $R^2$ are selected, independently, from hydrogen and $(C_1-C_4)$alkyl, and (iii) ring B is mono- or disubstituted with, respectively, one or two halo groups;

and the pharmaceutically acceptable salts thereof.

The present invention also relates to a pharmaceutical composition for treating a disorder or condition selected from hypertension, depression (e.g, depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (eg., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising an amount of a compound of the formula I or a pharmaceutically acceptable salt thereof effective in treating such disorder or condition and a pharmaceutically acceptable carrier.

The present invention also relates to a pharmaceutical composition for treating a disorder or condition that can be treated by inhibiting the reuptake of serotonin, dopamine or norepinephrine in a mammal, preferably a human, comprising an amount of a compound of the formula I, or a pharmaceutically acceptable salt thereof, that is effective in treating such disorder or condition and a pharmaceutically acceptable carrier. Examples of such disorders and conditions are those enumerated in the preceding paragraph.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (eg., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising administering to a mammal in need of such treatment an amount of a compound of the formula I, or a pharmaceutically acceptable salt thereof, that is effective in treating such disorder or condition.

The present invention also relates to a method for treating a disorder or condition that can be treated by inhibiting the reuptake of serotonin, dopamine or norepinephrine in a mammal, preferably a human, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising a serotonin, dopamine or norepinephrine reuptake inhibiting effective amount of a compound of the formula I, or a pharmaceutically acceptable salt thereof, and a pharmaceutically acceptable carrier.

The present invention also relates to a pharmaceutical composition for treating a disorder or condition that can be treated by inhibiting the reuptake of serotonin, norepinephrine or dopamine in a mammal, preferably a human, comprising serotonin, dopamine or norepinephrine reuptake inhibiting effective amount of a compound of the formula I, or a pharmaceutically acceptable salt thereof, and a pharmaceutically acceptable carrier.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising administering to a mammal requiring such treatment a serotonin, dopamine or norepinephrine reuptake inhibiting effective amount of a compound of the formula I, or a pharmaceutically acceptable salt thereof.

The present invention also relates to a method for treating a disorder or condition that can be treated by inhibiting the reuptake of serotonin, norepinephrine or dopamine in a mammal, preferably a human, comprising administering to a mammal requiring such treatment a serotonin, dopamine or norepinephrine reuptake inhibiting effective amount of a compound of the formula I, or a pharmaceutically acceptable salt thereof.

The present invention relates to a pharmaceutical composition for treating a condition or disorder that can be treated by inhibiting the reuptake of serotonin, dopamine or norepinephrine in a mammal, preferably a human, comprising:

a) a pharmaceutically acceptable carrier;
b) a compound of the formula I or a pharmaceutically acceptable salt thereof; and
c) an NK-1 receptor antagonist or a $5HT_{1D}$ receptor antagonist, or a pharmaceutically acceptable salt thereof;
wherein the amount of the active compounds (i.e., the compound of formula I and the NK-1 receptor antagonist or $5HT_{1D}$ receptor antagonist) are such that the combination is effective in treating such disorder or condition.

The present invention also relates to a method for treating a disorder or condition that can be treated by inhibiting the reuptake of serotonin, dopamine or norepinephrine in a mammal, preferably a human, comprising administering to a mammal requiring such treatment:

a) a compound of the formula I, defined above, or a pharmaceutically acceptable salt thereof; and
b) an NK-1 receptor antagonist or a $5HT_{1D}$ receptor antagonist, or a pharmaceutically acceptable salt thereof;
wherein the amounts of the active compounds (i.e., the compound of formula I and the NK-1 receptor antagonist or $5HT_{1D}$ receptor antagonist) are such that the combination is effective in treating such disorder or condition.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

The present invention also relates to all radiolabelled forms of the compounds of the formula I. Preferred radiolabelled compounds of formula I are those wherein the radiolabels are selected from as $^3H$, $^{11}C$, $^{14}C$, $^{18}F$, $^{123}I$ and $^{125}I$. Such radiolabelled compounds are useful as research and diagnostic tools in metabolism pharmacokinetics studies and in binding assays in both animals and man.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

Preferred embodiments of this invention include the following compounds of the formula I and their pharmaceutically acceptable salts:

[2-(3,4-Dichlorophenoxy)-5-fluorobenzyl]-dimethylamine;

[2-(3,4-Dichlorophenoxy)-5-fluorobenzyl]-methylamine;

[2-(3,4-Dichlorophenoxy)-5-trifluoromethylbenzyl]-dimethylamine;

N-[4-(3,4-Dichlorophenoxy)-3-dimethylaminomethylphenyl]-acetamide;

{1-[2-(3,4-Dichlorophenoxy)phenyl]-ethyl}-dimethylamine;

[2-(3,4-Dichlorophenoxy)-4-trifluoromethylbenzyl]-dimethylamine;

[2-(3,4-Dichlorophenoxy)-4-trifluoromethylbenzyl]-methylamine;

[4-Chloro-2-(3,4-dichlorophenoxy)-benzyl]-methylamine;

{1-[2-(3,4-Dichlorophenoxy)-5-fluorophenyl]-ethyl}-methylamine;

{1-[2-(3,4-Dichlorophenoxy)phenyl}-ethyl}-methylamine;
{1-[2-(4-Chlorophenoxy)phenyl]ethyl}-methylamine;
[2-(3,4-Dichlorophenoxy)-5-methoxybenzyl]-methylamine;
[2-(4-Chlorophenoxy)-5-fluorobenzyl]-methylamine; and
{1-[2-(4-Chlorophenoxy)-5-fluorophenyl]-ethyl}-methylamine;
[2-(3,4-Dichlorophenoxy)-5-methylbenzyl]-dimethylamine;
[4-Bromo-2-(3,4-dichlorophenoxy)-benzyl]-methylamine;
[5-Bromo-2-(3,4-dichlorophenoxy)-benzyl]-methylamine;
[2-(3,4-Dichlorophenoxy)-4,5-dimethoxybenzyl]-methylamine;
[2-(3,4-Dichlorophenoxy)-4-methoxybenzyl]-dimethylamine;
4-(3,4-Dichlorophenoxy)-3-methylaminomethyl-benzonitrile;
[2-(3,4-Dichlorophenoxy)-4,5-dimethylbenzyl]-methylamine;
3-(3,4-Dichlorphenoxy)-4-methylaminomethyl-benzonitrile;
(+)-{1-[2-(3,4-Dichlorophenoxy)-5-fluorophenyl]-ethyl}-methylamine;
(−)-{1-[2-(3,4-Dichlorophenoxy)-5-fluorophenyl]-ethyl}-methylamine;
[2-(3,4-Dichlorophenoxy)-5-trifluoromethyl-benzyl]-methylamine;
[2-(3,4-Dichlorophenoxy)-4-methoxybenzyl]-methylamine;
[2-(4-Chloro-3-fluorophenoxy)-5-fluorobenzyl]-methylamine;
[2-(3-Chloro-4-fluorophenoxy)-5-fluorobenzyl]-methylamine;
(+/−)-2-[2-(3,4-Dichlorophenoxy)-5-fluorophenyl]-pyrrolidine;
(−)-2-[2-(3,4-Dichlorophenoxy)-5-fluorophenyl]-pyrrolidine;
(+)-2-[2-(3,4-Dichlorophenoxy)-5-fluorophenyl]-pyrrolidine; and
2-[2-(3,4-Dichlorophenoxy)-5-fluorophenyl]-N-methylpyrrolidine.

Other embodiments of this invention include the following compounds and their pharmaceutically acceptable salts:

{1-[2-(3,4-Dichlorophenoxy)-5-fluorophenyl]-1-methylethyl}-methylamine;
{1-[2-(3,4-Dichlorophenoxy)-5-fluorophenyl]-1-methylethyl}-dimethylamine;
[4-Chloro-2-(4-chlorophenoxy)-5-fluorobenzyl]-methylamine;
[2-(3,4-Dichlorophenoxy)-5-fluoro-4-methoxybenzyl]-methylamine;
[4-(3,4-Dichlorophenoxy)-3-(dimethylaminomethyl)-phenyl]-dimethylamine
[5-Fluoro-2-(4-fluoro-3-methoxyphenoxy)-benzyl]-dimethylamine;
[2-(4-Chlorophenoxy)-5-isopropylbenzyl]-methylamine;
{1-[2-(4-Chlorophenoxy)-5-trifluoromethylphenyl]-ethyl}-methylamine;
[2-(4-Chlorophenoxy)-4,5-dimethylbenzyl]-methylamine;
{1-[5-Chloro-2(3,4-dichlorophenoxy)phenyl]-propyl}-methylamine;
[2-(3,4-Dichlorophenoxy)-5-methylsulfanyl-benzyl]-methylamine;
{1-[2-(3,4-Dichlorophenoxy)-5-methylsulfanyl-phenyl]-ethyl}-methylamine;
{1-[2-(3,4-Dichloro-phenoxy)-5-methylsulfanyl-phenyl]-1-methylethyl}-methylamine;
[2-(3,4-Dichlorophenoxy)-5-methylsulfanyl-benzyl]-dimethylamine;
[2-(3,4-Dichlorophenoxy)-5-methanesulfinyl-benzyl]-dimethylamine;
[2-(3,4-Dichlorophenoxy)-5-methanesulfinyl-benzyl]-methylamine;
[2-(3,4-Dichlorophenoxy)-5-methanesulfonyl-benzyl]-methylamine;
[2-(3,4-Dichlorophenoxy)-5-methanesulfonyl-benzyl]-dimethylamine;
[2-(3,4-Dichlorophenoxy)-5-(propane-2-sulfonyl)-benzyl]-methylamine;
2-[2-(3,4-Dichlorophenoxy)-5-fluorophenyl]-piperidine;
2-[2-(3,4-Dichlorophenoxy)-5-fluorophenyl]-1-methyl-piperidine;
3-[2-(3,4-Dichlor-phenoxy)-5-fluorophenyl]-4-methyl-morpholine;
2-[2-(3,4-Dichlorophenoxy)-5-fluorophenyl]-1,2-dimethyl-piperidine;
{1-[2-(3,4-Dichlorophenoxy)-5-fluorophenyl]-cyclopropyl}-dimethylamine;
2-[2-(3,4-Dichlorophenoxy)-5-fluorophenyl]-1,5-dimethyl-pyrrolidine;
3-[2-(3,4-Dichlorophenoxy)-5-fluorophenyl]-4-methyl-thiomorpholine;
{1-[2-(3,4-Dichlorophenoxy)-5-fluorophenyl]-cyclopentyl}-methylamine;
{1-[2-(3,4-Dichlorophenoxy)-5-(propane-2-sulfonyl)-phenyl]-ethyl-methylamine; and
[4-Chloro-2-(3,4-dichlorophenoxy)-5-methanesulfonyl-benzyl]-methylamine.

Other embodiments of this invention relate to the compound of the formula I wherein m is zero, n is one, $R^3$ and $R^4$ are hydrogen, X is chloro, bromo, iodo or methyl, $R^1$ is hydrogen and $R^2$ is methyl.

This invention also relates to compounds of the formula

XVIII

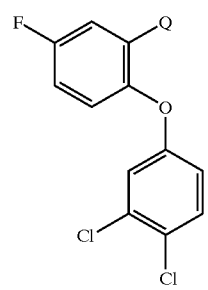

wherein Q is —C(=O)H, cyano, —C(=O)OH or —C(=O)NR¹R² wherein R¹ and R² are selected, independently, from hydrogen and (C₁-C₄)alkyl, or R¹ and R², together with the nitrogen to which they are attached, form a four to eight membered saturated ring containing one or two heteroatoms, including the nitrogen to which R¹ and R² are attached, wherein the second heteroatom, when present, is selected from oxygen, nitrogen and sulfur. These compounds are useful as intermediates in the synthesis of certain compounds of the formula I.

The compounds of formula XVIII may have optical centers and therefore may occur in different enantiomeric configurations. The invention includes all enantiomers, diastereomers, and other stereoisomers of such compounds of formula XVIII, as well as racemic and other mixtures thereof.

DETAILED DESCRIPTION OF THE INVENTION

Compounds of the formula I may be prepared according to the following reaction Schemes and discussion. Unless otherwise indicated, A, B, R¹, R², R³, R⁴, R⁵, R⁶, X, Y, m and n, and structural formulas I and XVIII, in the reaction schemes and discussion that follows are as defined above.

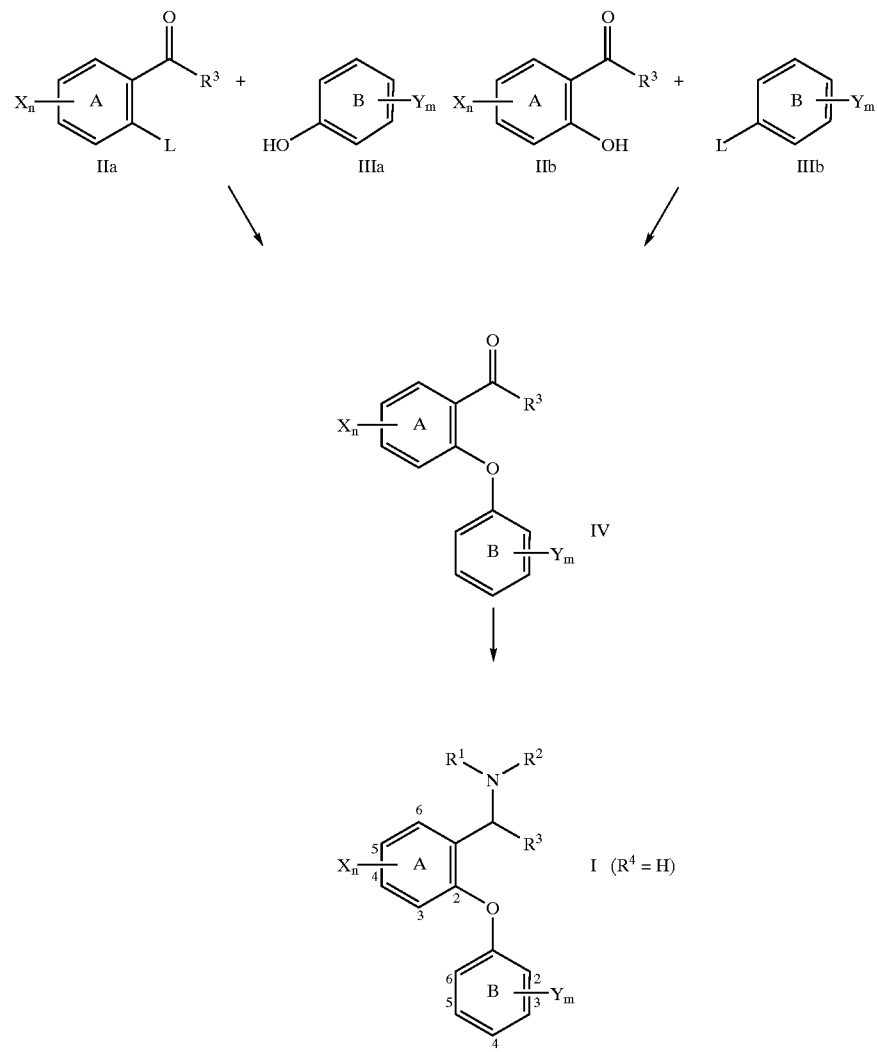

SCHEME 2
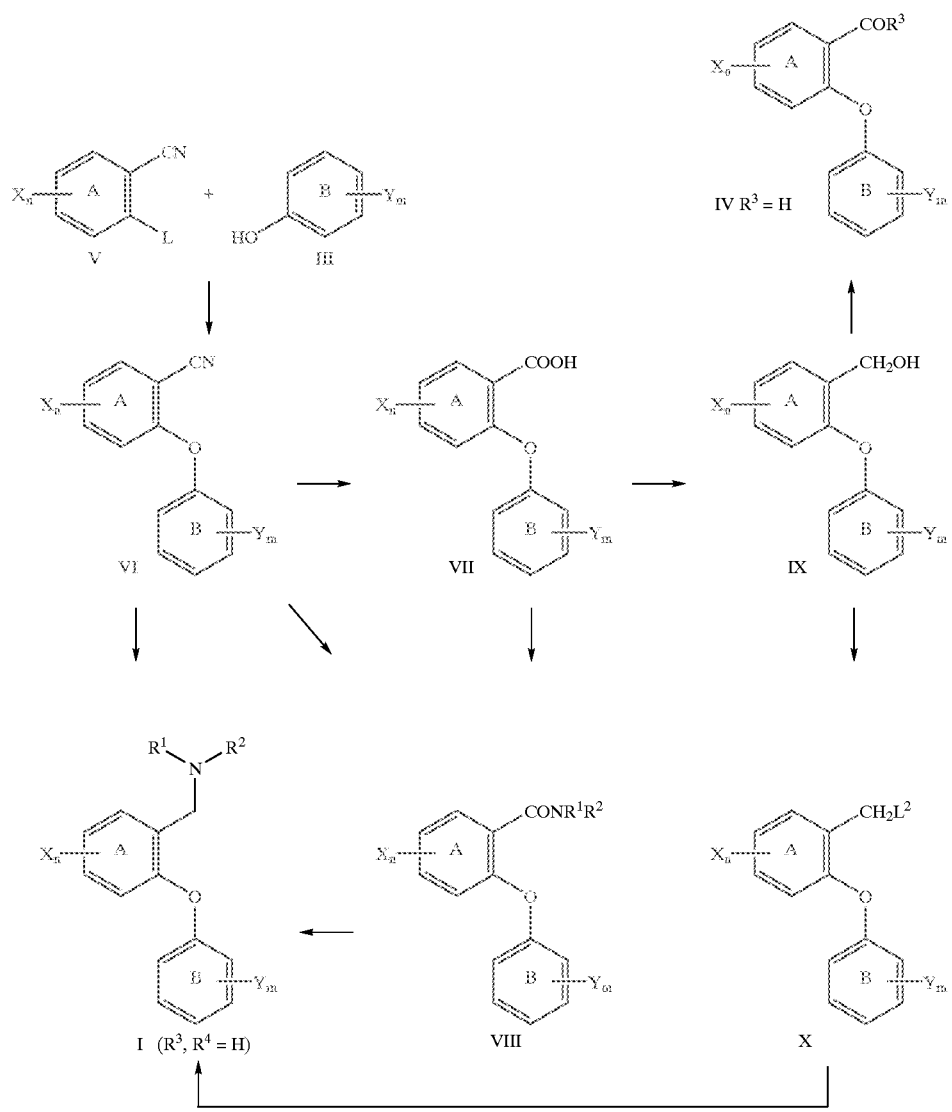
SCHEME 3
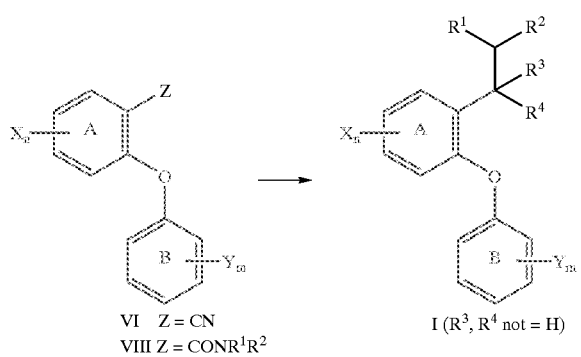
SCHEME 4
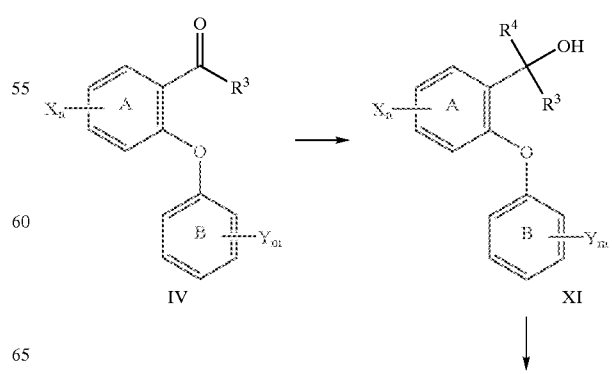

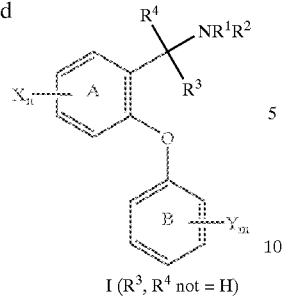

I ($R^3$, $R^4$ not = H)

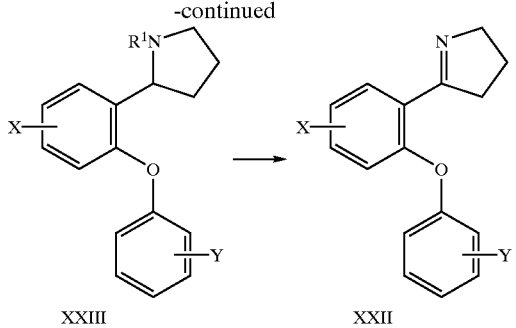

XXIII      XXII

SCHEME 5

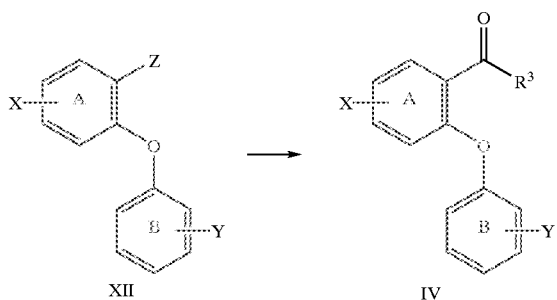

XII      IV

SCHEME 6

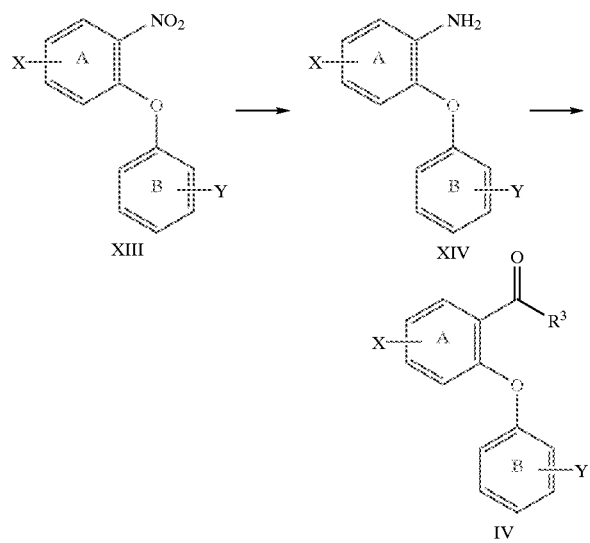

XIII      XIV

IV

SCHEME 7

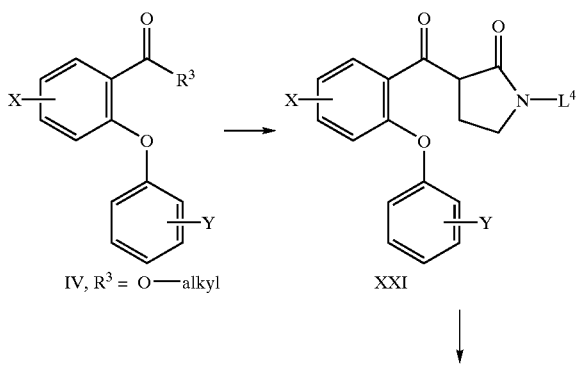

IV, $R^3$ = O—alkyl      XXI

Scheme 1 refers to the preparation of compounds of the formula I from compounds of the formulas II and III. Compounds of the formulas II and III are commercially available or can be made by methods well known to those of ordinary skill in the art. For example, compounds of general formulas IIa and IIb wherein $R^3$ is H may be prepared by introducing an aldehyde functional group (CHO) to a compound of formula XV or XVI, respectively, using methods well known to those of skill in the art.

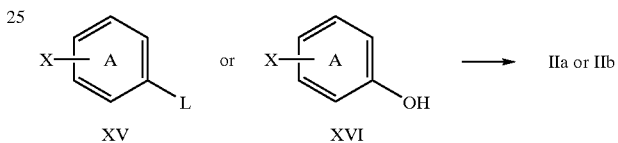

XV      XVI

When L=F, the procedure of A. J. Bridges et al., *Tetrahedron Letters*, 1992, 33(49), 7499–7502, is particularly useful for the synthesis of substituted ortho-fluorobenzaldehydes. Other such transformations have been described by C. F. H. Allen et al., *Organic Synthesis*, 1951, 31, 92; T. DePaulis et al, *J. Med. Chem.*, 1986, 29, 61; I. M. Godfrey et al., *J. Chemical Society, Perkin Transactions 1*, 1974, 1353; K. M. Tramposil et al., *J. Med. Chem.*, 1983, 26(2), 121; and M. E. Cracknell et al., *Chem. Ind., (London)*, 1985, (9), 309.

Referring to Scheme 1, a compound (i.e., an aldehyde or ketone) of the formula IIa, wherein L is a suitable leaving group such as fluoro, chloro, nitro or triflate, is reacted with a compound (i.e., a phenol) of the formula IIIa in the presence of a base to form the corresponding compound of formula IV. This reaction is generally carried out at a temperature from about 0° C. to about 150° C. for about 1 hour to about 3 days, preferably at about 90–95° C. for about 18 hours, in a polar solvent such as dimethyl sulfoxide (DMSO), N,N-dimethylformamide (DMF), N,N-dimethylacetamide (DMA) or N-methyl-2-pyrrolidinone (NMP), preferably DMF. Suitable bases include anhydrous sodium carbonate ($Na_2CO_3$), potassium carbonate ($K_2CO_3$), sodium hydroxide (NaOH), potassium hydroxide (KOH) and amines such as pyrrolidine, triethylamine and pyridine, with anhydrous $K_2CO_3$ being preferred. Details for conducting this procedure can be found in G. W. Yeager et al., *Synthesis*, 1995, 28–30; J. R. Dimmock et al., *Journal of Medicinal Chemistry*, 1996, 39(20), 3984–3997. Alternatively, phenols of the formula IIb and compounds of the formula IIIb may be converted into aldehydes or ketones of the general formulae IV according to the procedures described by K Tomisawa et al., *Chemical and Pharmaceutical Bulletin*, 1984, 32(8), 3066–3074.

Compounds of the formula IV can be converted into compounds of the formula I by subjecting them to reductive amination conditions. For example, a compound of the formula IV can be reacted with a compound of the formula HNR$^1$R$^2$ to form an intermediate of the formula XVII:

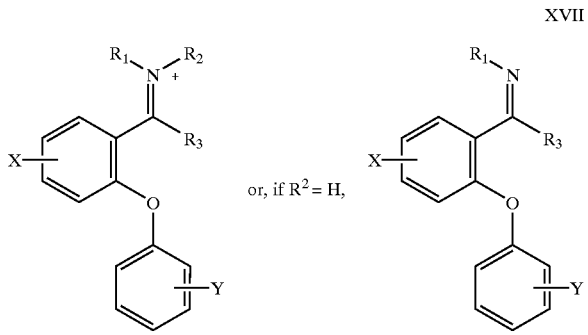

which may be isolated or converted directly in the same reaction step into a compound of the formula I. This conversion, whether in situ or starting with the isolated compound of formula XVII, can be performed using one or more methods known to those skilled in the art.

For example, the compound of formula IV and the appropriate compound of formula HNR$^1$R$^2$ can be combined in the presence of a dehydrating reagent such as titanium (IV) tetrachloride or titanium (IV) isopropoxide, in a reaction inert solvent such as benzene, toluene, ethanol or a like solvent, until the reaction is judged to be complete, according to the procedure of S. Bhattarcharyya (*Journal of Organic Chemistry*, 1995, 60(15), 4928–4929). Alternatively, the compound of formula IV and the compound of formula HNR$^1$R$^2$ can be combined in an inert solvent such as benzene or toluene, in the presence or absence of a water scavenger such as molecular sieves, and heated to eliminate water generated during the formation of the intermediate of formula XVII. The degree of completion of the conversion of compounds of the formula IV into the above intermediate(s) of formula XVII can be assessed using one or more known analytical techniques, including $^1$H-NMR spectroscopy.

In some instances, it may be possible or desirable to isolate the intermediate(s) of formula XVII, or they may be further reacted with a reducing agent selective for the reduction of the intermediate to the desired compounds of formula I. Such reducing agents are widely known to those skilled in the art and include, for example, sodium borohydride (NaBH$_4$), sodium cyanoborohydride (NaBH$_3$CN) and sodium triacetoxy-borohydride (NaBH(OAc)$_3$), as described by A. F. Abdel-Magid et al. in *Tetrahedron Letters*, 1990, 31, 5595). This reduction is generally carried out in a polar solvent such as methanol, ethanol, isopropanol or a like solvent, and at temperatures of about 0° C. to about 100° C., preferably at room temperature. In the procedure described by Bhattarcharyya, the intermediate of formula XVII is formed in an ethanol solvent and, without isolation, is reduced to the product of formula I using NaBH$_4$. As an alternative to the aldehyde or ketone intermediates of formula IV, one skilled in the art can also prepare compounds of formula VI (i.e., nitrites), as illustrated in Scheme 2, for use as intermediates in the syntheses of the desired compounds of formula I, using a diphenyl ether formation procedure analogous to that described in Scheme 1. Procedures for preparation of compounds of formula VI can be adapted from those found in the literature. (See, e.g., D. C. Remy et al., *J. Med. Chem.*, 1975, 18(2), 142–148; E. A. Schmittling et al., *Journal of Organic Chemistry*, 1993, 58(12), 3229–3230).

The conversion of the nitrites of formula VI so obtained into the desired products of formula I can be achieved by several routes, as depicted in Scheme 2. For example, the nitrile group of VI can be hydrolyzed under acidic conditions using methods well known to those of skill in the art, to produce a carboxylic acid derivative of formula VII. (See, e.g., A. I. Meyers et al., *Tetrahedron Letters*, 1984, 25 (28), 2941; and R. W. Higgins et al., *J. Organic Chemistry*, 1951, 16, 1275). This carboxylic acid derivative, in turn, can be converted into a carboxamide derivative having the formula VIII using one or more standard methods which are disclosed in the chemical literature, e.g., via reaction of an acid halide prepared from compounds of the formula VII with an amine of general formula HNR$^1$R$^2$. (See R. E. Kent et al., *Organic Synthesis*, Coll. Vol. III, 1955, 490; and R. M. Herbst et al., *Organic Synthesis*, Coll, Vol. II, 1943, 11 for discussions of the Schotten-Bauman reaction). The resulting carboxamides of the formula VIII, wherein R$^1$ and R$^2$ are hydrogen, can also be prepared directly from the corresponding nitrites of formula VI by specific hydrolysis methods, employing, for example, hydrogen peroxide or strong aqueous alkalis metal salts. (See *Chemistry & Industry*, 1961, 1987; C. R. Noller, *Organic Synthesis*, Coll. Vol. II, 1943, 586; and J. H. Hall and M. Gisler, *J. Organic Chemistry*, 1976, 41, 3769). Subsequently, the carboxamide derivatives of formula VIII may can be reduced using one of a variety of reducing agents available for such conversion, to produce the desired compounds of formula I. (See, e.g., A. C. Cope et al., *Organic Synthesis*, Coll. Vol. IV, 1963, 339, for use of lithium aluminum hydride in a diethyl ether or THF solvent.) Alternatively, the nitriles of formula VI can be reduced to form the desired compounds of general formula I, wherein R$^1$ and R$^2$ are hydrogen, by using one of a variety of reducing agents disclosed in the chemical literature which are selective for this transformation (including catalytic hydrogenation using hydrogen gas and platinum (II) oxide, as described by J. A. Secrist, III and M. W. Logue in *J. Organic Chemistry*, 1972, 37, 335; hydrazine hydrate and Raney nickel in ethanol, as described by W. W. Zajac, Jr. et al. in *J. Organic Chemistry*, 1971, 36, 3539; and sodium trifluoroacetoxy borohydride in THF, as described by N. Umino et al. in *Tetrahedron Letters*, 1976, 2875). Such reducing agents can also include lithium aluminum hydride in a nonreactive solvent such as diethyl ether or tetrahydrofuran.

Finally, the nitriles of formula VI may be converted to the corresponding aldehydes of general formula IV, wherein R$^3$ is hydrogen, using reaction conditions specific for this transformation, such as lithium triethoxyaluminum hydride in a solvent such as THF or diethyl ether, as described by H. C. Brown and C. P. Garg in *J. American Chemical Society*, 1964, 86, 1085 and by J. Malek and M. Cerny in *Synthesis*, 1972, 217.

Using an alternative synthetic pathway, the intermediate carboxylic acids of formula VII (or their methyl or ethyl ester derivatives) can be reduced to their corresponding benzylic alcohols of formula IX. This process is well precedented in the literature and can be accomplished using selective reducing agents such as sodium borohydride (see, e.g., J. V. B. Kanth et al., *J. Organic Chemistry*, 1991, 56, 5964), diborane in THF (see, e.g., M. N. Moon et al., *J. Organic Chemistry*, 1973, 38, 2786), and similar reducing agents.

The alcohols of formula IX so obtained can then be selectively re-oxidized to form the corresponding aldehydes of formula IV (R$^3$=H), for example, using pyridinium chlorochromate in methylene chloride, according to the procedure of E. J. Corey et al., *Tetrahedron Letters*, 1975, 31, 2647–2650, or C.-G. Huang, *Journal of Organic Chemistry*, 1991, 56(16), 4846–4853. The hydroxyl group of the compound of formula IX may be also converted into a more reactive leaving group $L^2$ (e.g., mesylate, triflate), as described in the scientific literature (see, e.g., M. S. Newman et al., J. Organic Chemistry, 1974, 39, 1036; and E. K. Anderson et al., *Synthesis*, 1974, 665), to generate intermediates of the formula X, which can then be reacted with the appropriate amines of formula $HNR^1R^2$ to produce the corresponding desired compounds of formula I.

Schemes 3 and 4 illustrate processes that can be used to introduce substituents ($R^3$, $R^4$) at the alpha position of the benzylamine side chain. In Scheme 3, according to the procedure of D. J. Calderwood et al., (*Tetrahedron Letters*, 1997, 38(7), 1241–1244), a nitrile of the formula VI or an amide of the formula VIII can be treated with a reagent of the formula $R^3MJ_2$ (wherein M is a metal such as cerium and J is a halogen such a Cl or Br) to produce a compound of the formula I wherein $R^1=R^2$=hydrogen. Such compounds can then be converted to compounds of formula I wherein $R^1$ and $R^2$ are other than hydrogen, for example, via the reductive amination procedures described herein.

Alternatively, according to Scheme 4, intermediates of the formula IV can be reacted with, for example, a Grignard reagent (i.e., $R^4MgJ$) under well established conditions to generate the intermediate alcohols of formula XI. Such alcohols of formula XI may be converted in one of several manners. For example, the alcohol may be reacted with $NaN_3$ in aqueous DMF, replacing the OH in formula XI with $N_3$, according to the procedure of Sharpless et al., *Tetrahedron Letters*, 1996, 37(19), 3219–3222. The azide derivative thus formed can then be reduced to the primary amine of formula I ($R^1=R^2$=H) under a variety of conditions, for example, using hydrogen and barium sulfate in ethanol, (A. Guy et al., *Synthesis*, 1988, 11, 900–904), lithium aluminum hydride in ether (M. Saito et al., *Journal of Medicinal Chemistry*, 1980, 23(12), 1364) or tributyltin hydride in benzene (J. Wasserman et al, *Journal of American Chemical Society*, 1985, 107(2), 519). The primary amine (—$NH_2$) compound of formula I so obtained can be converted to compounds of formula I wherein $R^1$ and $R^2$ are other than hydrogen, as described previously.

In addition to the methods described above in Schemes 1 and 2 for the preparation of the intermediate aldehydes and ketones of formula IV, other methods exist which can provide compounds of the formula IV. For example, a compound of formula XII, in which the group Z is a hydrogen atom, can be reacted, under conditions of Friedel-Crafts acylation (e.g., $AlCl_3/CH_2Cl_2/R^3COCl$), to produce ketones of the formula IV in which $R^3$ is not hydrogen. This procedure is depicted in Scheme 5 and is well precedented in the scientific literature and familiar to those skilled in the art. The location of the acyl group ($COR^3$) can be determined by the nature and location of the X and/or Y substituents present, as well as the conditions employed for the reaction. In instances where it is desireable to prepare compounds of formula IV ($R^3$=H), from XII (Z=H), introduction of the aldehyde functional group (CHO) may be achieved using conditions described above for the preparation of the intermediates IIa and IIb in Scheme 1.

Preparation of compounds of the formula IV wherein $R_3$=H (i.e., aldehydes) can be achieved using one or more of the known procedures for the formylation of aromatic rings, including reacting dichloromethyl methyl ether and titanium (IV) tetrachloride in methylene chloride according to the procedure described by M. L. Mancini et al., *Synthetic Communications*, 1989, 2001–2007, or H. Chikashita et al., *J. Organic Chemistry*, 1991, 56, 1692.

Alternatively, reaction of the compounds of formula XII wherein Z is a halogen (e.g., Br, I) with a strong base (e.g., n-sec- or tert-butyl lithium, lithium diisopropylamide) in an inert solvent such as hexane or THF, followed by reaction with a reagent such as N,N-dimethylformamide (DMF), will produce aldehydes like those of formula IV. (See G. Voss et al., Chemishe Berichte, 1989, 122, 1199; M. P. Hoyer et al., *J. Organic Chemistry*, 1986, 51(26), 5106; and N. Eisen et al., *Angew. Chem. International Edition*, 1986, 25(11), 1026).

Another method for the preparation of compounds of formula IV relies on the oxidation of an alkyl group (e.g., $CH_3$, $C_2H_5$) at the Z position of compounds of the formula XII. The oxidation can progress to the formation of the aldehyde of the formula IV, wherein $R^3$=H (e.g., F. M. Hauser et al., *Synthesis*, 1987, 723; S. D. Carter et al., *Synthesis*, 1983, (12), 1000; European Patent 451650, 1991, Bayer AG), or, under more vigorous conditions, can proceed to the formation of a carboxylic acid compound of formula VII, from which it can then be converted into compounds of the formula I, as depicted in Scheme 2. The success of this oxidation procedure will, of course, depend upon the nature and location of any additional substituents X and Y on the compounds of formula XII.

Yet another alternative for the preparation of the intermediates of formula IV is illustrated by Scheme 6. Compounds of the formula XII, containing a nitro group and prepared according to procedures described by R. Beugelmans et al. (*Tetrahedron Letters*, 1994, 35(31), 5649–5652), J. H. Clark et al., (*Tetrahedron Letters*, 1987, 28(31), 3627) and E. Roberts et al., (*Journal of the Chemical Society*, 1925, 127, 2004), can be reduced under conditions disclosed in the chemical literature to the corresponding amine compounds of formula XIV. There reductions can be accomplished using gaseous hydrogen ($H_2$) and a catalyst (e.g., Pd/C, Raney nickel) in an alcohol solvent such as ethanol, at pressures of about one to about 5 atmospheres of $H_2$, or using an in situ reduction using an iron/acetic acid or tin/hydrochloric acid system to produce the corresponding compounds of formula XIV. These latter intermediates of formula XIV can then be converted, via their diazonium salts (prepared, for example, using $NaNO_2$ and aqueous HCl) into the nitriles of formula VI (i.e. see H. T Clarke and R. R. Read, *Organic Synthesis*, 1941, 514) which may then be converted via the corresponding carboxylic acids of formula VII as shown in Scheme 2 into aldehydes of the general formula IV wherein $R^3$=H.

The intermediates of formula XIV can also be converted directly into the corresponding aldehydes of formula IV by reacting them with formaldoxime, followed by acid hydrolysis, as described by R. B. Woodward et al., *Tetrahedron*, 1958, 2, 1 and W. F. Beech in *J. Chemical Society*, 1954, 1297.

For the preparation of compounds of the general formula I wherein $R^2$ and $R^3$ taken together with the nitrogen to which $R^2$ is attached and the carbon to which $R^3$ is attached form a nitrogen containing ring, an adaptation of the procedure described by L. S. Bleicher et al (J. Organic Chemistry, 1998, 63, 1109) can be employed, as shown in Scheme 7. Thus, an ester of the general formula IV ($R^3$=O-alkyl) is reacted with a cyclic lactam of the general formula XXX

XXX

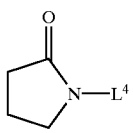

where $L^4$ is a reaction labile group such as —CH=CH$_2$, in the presence of a strong base such as sodium methoxide, to produce the intermediate of general formula XXI. This intermediate can then be converted to the corresponding cyclic imine of formula XXII in the presence of a strong acid, such as hydrochloric acid, usually under reflux conditions. Subsequently, the compounds of formula XXII can be reduced to form the cyclic amines of formula XXIII (wherein $R^1$=H) using, for example, sodium borohydride in methanol as described previously. Such compounds of formula XXIII can further be converted into compounds of the formula XXIII (wherein $R^1$ is as defined for compounds of formula I) as previously discussed.

Pharmaceutically acceptable salts of a compound of formula I can be prepared in a conventional manner by treating a solution or suspension of the corresponding free base or acid with one chemical equivalent of a pharmaceutically acceptable acid or base. Conventional concentration or crystallization techniques can be employed to isolate the salts Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously or rectally) or topically. In general, the daily dosage for treating a disorder or condition according to the methods described above will generally range from about 0.01 to about 10.0 mg/kg body weight of the patient to be treated. As an example, a compound of the formula I or a pharmaceutically acceptable salt thereof can be administered for treatment of, for example, depression to an adult human of average weight (about 70 kg) in a dose ranging from about 0.7 mg up to about 700 mg per day, preferably from about 1 mg to about 500 mg per day, in single or divided (i.e., multiple) portions. Variations based on the aforementioned dosage ranges may be made by a physician of ordinary skill taking into account known considerations such as the weight, age, and condition of the person being treated, the severity of the affliction, and the particular route of administration chosen.

The in vitro activity of the compounds of the present invention at the individual monoamine reuptake sites can be determined using rat synaptosomes or HEK-293 cells transfected with the human serotonin, dopamine or norepinephrine transporter, according to the following procedure adapted from those described by S. Snyder et al., (*Molecular Pharmacology*, 1971, 7, 66–80), D. T. Wong et al., (*Biochemical Pharmacology*, 1973, 22, 311–322), H. F. Bradford (*Journal of Neurochemistry*, 1969, 16, 675–684) and D. J. K. Balfour (*European Journal of Pharmacology*, 1973, 23, 19–26).

Synaptosomes: Male Sprague Dawley rats are decapitated and the brains rapidly removed. The cortex, hippocampi and corpus striata are dissected out and placed in ice cold sucrose buffer, 1 gram in 20 ml of buffer (the buffer is prepared using 320 mM sucrose containing 1 mg/ml glucose, 0.1 mM ethylenediamine tetraacetic acid (EDTA) adjusted to pH 7.4 with tris(hydroxymethyl)-aminomethane (TRIS) base). The tissues are homogenized in a glass homogenizing tube with a Teflon™ pestle at 350 rpm using a Potters homogenizer. The homogenate is centrifuged at 1000×g for 10 min. at 4° C. The resulting supernatant is recentrifuged at 17,000×g for 20 min. at 4° C. The final pellet is resuspended in an appropriate volume of sucrose buffer that yielded less than 10% uptake.

Cell Preparation: HEK-293 cells transfected with the human serotonin (5-HT), norepinephrine (NE) or dopamine (DA) transporter are grown in DMEM (Dulbecco's Modified Eagle Medium, Life Technologies Inc., 9800 Medical Center Dr., Gaithersburg, Md., catalog no. 11995-065)) supplemented with 10% dialyzed FBS (Fetal Bovine Serum, from Life Technologies, catalog no. 26300-053), 2 mM L-glutamine and 250 ug/ml G418 for the 5-HT and NE transporter or 2 ug/ml puromycin for the DA transporter, for selection pressure. The cells are grown in Gibco triple flasks, harvested with Phosphate Buffered Saline (Life Technologies, catalog no. 14190-136) and diluted to an appropriate amount to yield less than 10% uptake.

Neurotransmitter Uptake Assay: The uptake assays are conducted in glass tubes containing 50 uL of solvent, inhibitor or 10uM sertraline, desipramine or nomifensine for the 5-HT, NE or DA assay nonspecific uptake, respectively. Each tube contains 400 uL of [3H]5-HT (5 nM final), [3H]NE (10 nM final) or [3H]DA (5 nM final) made up in modified Krebs solution containing 100 uM pargyline and glucose (1 mg/ml). The tubes are placed on ice and 50 uL of synaptosomes or cells is added to each tube. The tubes are then incubated at 37° C. for 7 min. (5-HT, DA) or 10 min. (NE). The incubation is terminated by filtration (GF/B filters), using a 96-well Brandel Cell Harvester, the filters are washed with modified Krebs buffer and counted using either a Wallac Model 1214 or Wallac Beta Plate Model 1205 scintillation counter.

EXPERIMENTAL EXAMPLES

Preparation 1

2-(3,4-Dichlorophenoxy)-5-Trifluoromethylbenzaldehyde

Under $N_2$ in a 50 mL round-bottomed flask fitted with a reflux condenser and magnetic stirrer were placed 0.829 g (6.0 mmol) of $K_2CO_3$ and 0.342 g (2.1 mmol) of 3,4-dichlorophenol (Aldrich Chem. Co., Milwaukee, Wis.) in 10 mL of anhydrous N,N-dimethylformamide (DMF). After stirring the mixture for 5 min., 0.384 g (2.0 mmol) of 2-fluoro-5-trifluoromethylbenzaldehyde (Aldrich) was added and the mixture was heated to 90–95° C. overnight. After allowing the reaction to cool to room temperature, the mixture was diluted with water and EtOAc, the aqueous layer was extracted with additional EtOAc and the organic layers were combined, washed with $H_2O$ and saturated NaCl and dried over $MgSO_4$. Removal of the solvent in vacuo gave a light amber colored oil, 0680 g.

$^1$H-NMR (CDCl$_3$, 400 MHz): d 10.46 (s, 1H), 8.18 (s, 1H), 7.74 (m, 1H), 7.48 (m, 1H), 7.23 (m, 1H), 6.97 (m, 2H).

Mass spectrum (GCMS, m/z): 334 (m$^+$).

In the same manner, the following aldehyde and ketone intermediates of the formula IV were prepared:

| Prep. No. | $X_{(n)}$ | $Y_{(m)}$ | $R^3$ | yield (%) | m.p. (° C.) | m/z (m$^+$) | $^1$H-NMR (CDCl$_3$, δ) |
|---|---|---|---|---|---|---|---|
| 2 | H | 3,4-Cl$_2$ | H | 35 | 57–58 | 269, 267 | (s, 1H), 7.94(d, 1H), 7.56(m, 1H), 7.42(d, 1H), 7.24(m, 1H), 7.15 (s, 1H), 6.90(m, 2H). |
| 3 | 5-F | 4-Cl | H | 57 | oil | 252, 250 | (s, 1H), 7.58(dd, 1H), 7.33(m, 2H), 7.23(m, 1H), 6.95(m, 1H), 6.90 (dd, 1H). |
| 4 | H | 4-Cl | H | 71 | oil | 234, 232 | (s, 1H), 7.92(dd, 1H), 7.51(m, 1H), 7.33(m, 2H), 7.22(t, 1H), 7.00 (m, 2H), 6.87(dd, 1H). |
| 5 | 5-F | 3,4-Cl$_2$ | H | 67 | oil | 286, 284 | (d, 1H), 7.60(dd, 1H), 7.42(d, 1H), 7.28(m, 1H), 7.10(d, 1H), 6.95 (dd, 1H), 6.87(dd, 1H). |
| 6 | 5-F | 3,4-(OCH$_2$O) | H | 38 | oil | 270 | (s, 1H), 7.57(m, 1H), 7.20(m, 1H), 7.18(m, 1H), 7.04(d, 1H), 6.88 (m, 1H), 6.73(m, 2H), 2.72(m, 4H), 1.78(m, 4H). |
| 7 | 5-CF$_3$ | 3,4-Cl$_2$ | H | 98 | oil | 336, 334 | (s, 1H), 8.18(s, 1H), 7.74(m, 1H), 7.48(m, 1H), 7.23(m, 1H), 6.97 (m, 2H). |
| 8 | 5-NO$_2$ | 3,4-Cl$_2$ | H | 20 | oil | 313, 311 | (s, 1H), 8.78(d, 1H), 8.35(dd, 1H), 7.54(d, 1H), 7.25(m, 1H), 7.02 (dd, 1H), 6.94(d, 1H). |
| 9 | 3-CF$_3$ | 3,4-Cl$_2$ | H | 98 | oil | 336, 334 | (s, 1H), 8.16(dd, 1H), 7.99(dd, 1H), 7.54(t, 1H), 7.34(d, 1H), 6.92 (d, 1H), 6.6(dd, 1H). |
| 10 | H | 3,4-Cl$_2$ | CH$_3$ | 17 | oil | 284, 282 | (dd, 1H), 7.46(dt, 1H), 7.39(d, 1H), 7.24(dt, 1H), 7.21(d, 1H), 7.08 (d, 1H), 6.92(dd, 1H), 6.83(dd, 1H), 2.57(s, 3H). |
| 11 | H | 4-CH$_3$ | H | 69 | oil | 212 | (s, 1H), 7.46(m, 1H), 7.15 (m, 3H), 6.96(m, 2H), 6.84(d, 1H), 2.34 (s, 3H). |

-continued

| Prep. No. | X$_{(n)}$ | Y$_{(m)}$ | R$^3$ | yield (%) | m.p. (° C.) | m/z (m$^+$) | $^1$H-NMR (CDCl$_3$, δ) |
|---|---|---|---|---|---|---|---|
| 12 | 4-CF$_3$ | 3,4-Cl$_2$ | H | 44 | oil | 338, 336 | (s, 1H), 8.05(d, 1H), 7.49(d, 2H), 7.22(m, 1H), 7.13(s, 3H), 6.94 (dd, 1H). |
| 13 | H | 3,4-F$_2$ | H | 68 | oil | 234 | (s, 1H), 7.93(dd, 1H), 7.53 (dt, 1H), 7.23(d, 1H), 7.17(t, 1H), 6.89 (m, 2H), 6.78(m, 1H). |
| 14 | H | 4-CH$_3$ | CH3 | 19 | oil | 227 | (dd, 1H), 7.38(m, 1H), 7.13(m, 3H), 6.86(m, 3H), 2.63(s, 3H), 2.33 (s, 3H). |
| 15 | 6-CF$_3$ | 3,4-Cl$_2$ | H | 79 | oil | 336, 334 | (s, 1H), 7.59(m, 2H), 7.42(dd, 1H), 7.14(dd, 1H), 7.12(m, 1H), 6.87 (m, 1H). |
| 16 | 5-F | 3,4-(CH$_3$)$_2$ | H | 53 | oil | 244 | (s, 1H), 7.57(dd, 1H), 7.19(m, 1H), 7.11(d, 1H), 6.87(dd, 1H), 6.81 (m, 1H), 6.75(dd, 1H), 2.24(s, 6H). |
| 17 | H | 3,4-(CH3)$_2$ | H | 60 | oil | 226 | (s, 1H), 7.91(dd, 1H), 7.89 (d, 1H), 7.46(dt, 1H), 7.11(m, 2H), 6.85 (m, 2H), 6.79(dd, 1H), 2.24(s, 6H). |
| 18 | 4-CF$_3$ | 3,4-Cl$_2$ | H | 37 | oil | 336, 334 | (s, 1H), 8.04(d, 1H), 7.48(m, 2H), 7.20(s, 1H), 7.13(s, 1H), 6.94 (dd, 1H). |
| 19 | 4-Cl | 3,4-Cl$_2$ | H | 55 | oil | 302, 300 | (s, 1H), 7.86(d, 1H), 7.46(d, 1H), 7.19(m, 2H), 6.94(dd, 1H), 6.86 (d, 1H). |
| 20 | 5-F | 3,4-(OCH$_2$O) | H | 19 | oil | 260 | (s, 1H), 7.56(dd, 1H), 7.19(m, 1H), 6.86(dd, 1h), 6.77(d, 1H), 6.58 (s, 1H), 6.47(d, 1H), 5.99(s, 2H). |
| 21 | 3-F | 3,4-Cl$_2$ | H | 63 | foam | 286, 284 | (s 1H), 7.76(d, 1H), 7.41(m, 3H), 6.81(s, 1H), 6.80(s, 1H). |
| 22 | 5-F | 3,4-Cl$_2$ | CH$_3$ | 15 | foam | 300, 298 | (dd, 1H), 7.40(d, 1H), 7.20(m, 1H), 7.05(d, 1H), 6.94(dd, 1H), 6.80 (dd, 1H), 2.55(s, 3H). |
| 23 | 5-F | 4-Cl | CH$_3$ | 27 | foam | 266, 264 | (dd, 1H), 7.30(d, 2H), 7.15(dt, 1H), 6.89(d, 2H), 2.57(s, 3H). |
| 24 | 4-F | 3,4-Cl$_2$ | H | 41 | oil | 286, 284 | 10.2(s, 1H), 7.85(m, 1H), 7.47(d, 1H), 7.22 (d, 1H), 6.95(m, 1H), 6.82(m, 1H), 6.68(m, 1H). |
| 25 | 5-OCH$_3$ | 3,4-Cl$_2$ | H | 9 | oil | 298, 296 | (s, 1H), 7.38(m, 2H), 7.15(M, 1h), 7.05(S, 1h), 6.94(D, 1h), 6.83 (DD, 1h), 3.84(S, 3h). |
| 26 | H | 4-Cl | CH3 | 29 | oil | 248, 246 | (d, 1H), 7.43(dt, 1H), 7.31(s, 1H), 7.29(s, 1H), 7.21(t, 1H), 6.92 (d, 1H), 6.88(d, 1H), 2.60(s, 3H). |
| 27 | 5-F | 4-Cl | H | 60 | oil | 252, 250 | (s, 1H), 7.59(dd, 1H), 7.33(m, 2H), 7.23(m, 1H), 6.94(m, 3H). |
| 28 | 4,5-(OCH3)$_2$ | 3,4-Cl$_2$ | H | 40 | oil | 328, 326 | (s, 1H), 7.25(m, 1H), 7.07(dd, 1H), 6.95 (dd, 1H), 6.85(dd, 1H), 6.83(dd, 1H), 3.92(s, 3H), 3.85(s, 3H) |
| 29 | 4,5-(CH3)$_2$ | 3,4-Cl$_2$ | H | 29 | oil | 296, 294 | (s, 1H), 7.67(s, 1H), 7.38(d, 1H), 7.07(s, 1H), 6.85(m, 1H), 6 71 s, 1H), 2.26(d, 6H). |

-continued

| Prep. No. | $X_{(n)}$ | $Y_{(m)}$ | $R^3$ | yield (%) | m.p. (° C.) | m/z (m+) | $^1$H-NMR (CDCl$_3$, δ) |
|---|---|---|---|---|---|---|---|
| 30 | 5-Br | 3,4-Cl$_2$ | H | 90 | 129–132 | 346, 344 | 10.4(s, 1H), 8.03(d, 1H), 7.64(dd, 1H), 7.45 (dd, 1H), 7.15(d, 1H), 6.91(dd, 1H), 6.89(dd, 1H) |
| 31 | 4-Br | 3,4-Cl$_2$ | H | 47 | solid | 346, 344 | (s, 1H), 7.79(dd, 1H), 7.47(m, 1H), 7.37(m, 1H), 7.19(m, 1H), 7.03 (m, 1H), 6.94(m, 1H). |

Preparation 32

5-Cyano-2-(3,4-Dichlorophenoxy)-Benzaldehyde

Under N$_2$ in a flame-dried 3-neck round bottomed flask fitted with a reflux condenser and magnetic stirrer, a mixture of 5-bromo-2-(3,4-dichlorophenoxy)-benzaldehyde (3.0 g, 8.7 mmol), zinc (II) cyanide (1.5 g, 13 mmol) and tetrakis (triphenylphosphine) palladium (0) (1.5 g, 1.3 mmol) in anhydrous DMF (145 ml) was stirred at room temperature while degassing with N$_2$ for 5 min. After heating at approximately 80° C. for 90 min., the reaction was judged complete by thin layer chromatography (50% CH$_2$Cl$_2$:hexanes) and was allowed to cool to room temperature. The reaction mixture was then diluted with water and ethyl acetate (EA) and stirred another 10 min. The water layer was separated, extracted twice with EA and combined with the original EA layer, and washed with an aqueous solution of Rochelle salt (potassium sodium tartrate tetrahydrate) followed by aqueous NaCl. The organic layer was dried with Na$_2$SO$_4$, filtered and concentrated in vacuo to an oil. The oil was flash chromatographed on a 15×5 cm column of silica gel, eluting with CH$_2$Cl$_2$:hexanes (1:1) to obtain the title product as a white solid, 1.5 g (60%), m.p. 122–126° C.

Mass spectrum (GC/MS, m/z): 291 (m+), 262.

$^1$H-NMR (CDCl$_3$, d): 10.47 (s, 1H), 8.22 (d, 1H), 7.75 (dd, 1H), 7.53 (d, 1H), 7.25 (m, 1H), 6.98 (dd, 1H), 6.92 (d, 1H).

In the same manner, 4-cyano-2-(3,4-dichlorophenoxy)-benzaldehyde was prepared from the corresponding 4-bromo-2-(3,4-dichlorophenoxy)-benzaldehyde, clear oil, 16%. Mass spectrum (GC/MS, m/z): 291 (m+). $^1$H-nmr (CDCl$_3$, d): 10.45 (s, 1H), 8.02 (d, 1H), 7.55 (m, 2H), 7.23 (m, 1H), 7.14 (m, 1H), 6.96 (dd, 1H).

Preparation 33

4,5-Dimethoxy-2-Fluorobenzaldehyde

In a flame-dried, round-bottomed flask fitted with a magnetic stirrer and N$_2$ inlet was placed 4-fluoroveratrole (0.78 g, 5.0 mmol, Aldrich Chemical Co.) in 20 ml of anhydrous CH$_2$Cl$_2$. After cooling to 0° C., titanium (IV) chloride (0.91 ml, 1.57 g, 8.3 mmol) was added, followed after 10 min. by a,a-dichloromethyl methyl ether (0.45 ml, 0.575 g, 5.0 mmol). The mixture was allowed to warm to room temperature and after 2 hr it was quenched with an excess of aqueous saturated NaHCO$_3$. The suspension was filtered through a pad of d.e. (diatomaceous earth), the aqueous phase was extracted with additional amounts of CH$_2$Cl$_2$ and the organic phases were combined and washed with water followed by saturated aqueous NaCl. After drying with MgSO$_4$, the organic solvent was removed in vacuo to give the title compound as a white solid, 910 mg.

$^1$H-NMR (CDCl$_3$, d): 10.2 (s, 1H), 7.26 (d, 1H), 6.64 (d, 1H), 3.93 (s, 3H), 3.89 (s, 3H).

Preparation 34

2-(3,4-Dichlorophenoxy)-5-Benzonitrile

Under N$_2$ in a single-neck round bottomed flask with a reflux condenser and magnetic stirrer, a mixture of 3,4-dichlorophenol (1.96 g, 12 mmol) and anhydrous potassium carbonate (4.14 g, 30 mmol) in anhydrous N,N-dimethylformamide (DMF, 50 ml) was treated with 2,5-difluorobenzonitrile (1.39 g, 10 mmol, Aldrich Chemical Co., Milwaukee, Wis.) and heated to 95–100° C. for 18 hr. The mixture was then cooled to room temperature and diluted with water and ethyl acetate (EA), the water layer was extracted with additional quantities of EA and the EA layers were combined, washed with water, 2N NaOH, water and finally saturated aqueous NaCl. After drying over MgSO4, the solvent was removed in vacuo to give a tan solid.

Mass spectrum (GC/MS): m/z 281 (m+).

$^1$H-NMR (CDCl$_3$, 300 MHz, d): 7.43 (d, 1H), 7.37 (dd, 1H), 7.26 (m, 1H), 7.12 (d, 1H), 6.92 (m, 2H).

In a similar fashion, the following benzonitriles of the formula VI were prepared, isolated after flash chromatography (silica gel, elution with 20% CH$_2$Cl$_2$ in hexanes):

| Prep. No. | X | Y | Yield, % | m/z, m+ | $^1$H-NMR(CDCl$_3$, δ) |
|---|---|---|---|---|---|
| 35 | 5-CH$_3$ | 3,4-Cl$_2$ | 24 | 279, 277 | (bs, 1H), 7.40(d, 1H), 7.30(dd, 1H), 7.10(d, 1H), 6.87(m, 2H), 2.34(s, 3H). |
| 36 | 4-OCH$_3$ | 3,4-Cl$_2$ | 46 | 295, 293 | (d, 1H), 7.44(d, 1H), 7.17(d, 1H), 6.94(dd, 1H), 6.70(dd, 1H), 6.37(d, 1H), 3.78(s, 3H). |
| 37 | H | 3,4-Cl$_2$ | 98 | 265, 263 | (dd, 1H), 7.52(t, 1H), 7.44(d, 1H), 7.20(m, 2H), 6.92(m, 2H). |

Preparation 38

2-(3,4-Dichlorophenoxy)-5-Fluoro-N-Methyl-Benzamide

A mixture of 0.602 g (2.0 mmol) of 2-(3,4-dichlorophenoxy)-5-fluoro-benzoic acid in 20 mL of anhydrous benzene was treated with 2 drops of N,N-dimethylformamide (DMF), followed by slow addition of 0.785 μg (481 μL, 6.6 mmol) of thionyl chloride. After heating to reflux for 3.5 hr, the solution was stirred at room temperature overnight and concentrated in vacuo to a tan oil that was further azeotroped twice with fresh benzene. The residue was re-dissolved in 4 mL of benzene and added to 15 mL of 1.0 M $CH_3NH_2$ in $CH_3OH$ (Aldrich Chem. Co.) at 25° C. After 12 hr, the mixture was concentrated in vacuo and partitioned between water and EtOAc. The aqueous layer was then extracted with additional EtOAc and the combined organic extracts were washed with water followed by saturated aqueous NaCl, dried with $MgSO_4$, filtered and concentrated to a brown oil which slowly solidified on standing, 0.654 g.

$^1$H-nmr ($CDCl_3$, 400 MHz, δ): 7.89 (dd, 1H), 7.41 (d, 1h), 7.30 (bs, 1H, NH), 7.09 (m, 2H), 6.83 (m, 2H), 2.95 (d, 3H).

Preparation 39

2-(3,4-Dichlorophenoxy)-5-Fluoro-Benzonitrile

A flame-dried flask containing $N_2$ inlet and magnetic stirrer was charged with 2.9 g (18 mmol) of 3,4-dichlorophenol, 6.2 g (45 mmol) of potassium carbonate and 50 mL of anhydrous DMF. With stirring, 2.08 g (15 mmol) of 2,5-difluorobenzonitrile (Aldrich Chem. Co.) was added and the mixture was heated overnight at 105° C., cooled to room temperature and partitioned between water and EtOAc. The aqueous layer was reextracted with EtOAc and the combined organic layers were successively washed with 2N NaOH, water and saturated aqueous NaCl. After drying with MgSO4, the solvent was removed to give the title product as a light brown oil which slowly solidified, 3.5 g.

Mass spectrum (APCl, m/z): 281 (m$^+$).

$^1$H-nmr ($CDCl_3$, 400 MHz, δ): 7.43 (d, 1H), 7.37 (dd,1H), 7.26 (m, 1H), 7.12 (d, 1H), 6.92 (m, 2H).

Preparation 40

2-(3,4-Dichlorophenoxy)-5-Fluoro-Benzaldehyde

A flame-dried flask containing $N_2$ inlet and magnetic stirrer was charged with 1.24 g (9.0 mmol) of potassium carbonate and 20 mL of anhydrous DMF, followed by 0.513 g (3.15 mmol) of 3,4-dichlorophenol, with stirring at room temperature. After 5 min, 0.426 g (3.0 mmol) of 2,5-difluorobenzaldehyde (Aldrich Chem. Co.) was added and the mixture was heated at 95° C. for 18 hr. After cooling to room temperature, the mixture was diluted with water, twice extracted with EtOAc and the organic extracts were washed with water and saturated NaCl and dried over MgSO4. Removal of the solvent gave a brown oil, 963 mg, which was chromatographed on 230–400 mesh silica eluted with 5% EtOAc:95% hexanes.

The title product was isolated from the appropriate fractions as a white low-melting solid, 0.572 g.

$^1$H-nmr ($CDCl_3$, 400 MHz, δ): 7.60 (dd, 1H), 7.42 (d, 1H), 7.28 (m, 1H), 7.10 (d, 1H), 6.95 (dd, 1H), 6.87 (dd, 1H).

Example 1

2-Fluoro-6-(P-Tolyloxy)Benzylamine

A flame-dried flask containing $N_2$ inlet and magnetic stirrer was charged with 6.0 mL of 1.0 M lithium aluminum hydride in THF (6.0 mmol, Aldrich Chem. Co.), followed by an additional 10 mL of anhydrous THF at room temperature. While stirring, 0.341 g (1.5 mmol) of 2-fluoro-6-(p-tolyloxy)benzonitrile (Maybridge Chem. Co. Ltd., Trevillett, Tintagel, Cornwall, UK) was added slowly via syringe, causing some mild foaming. After 4 hr, a tlc ($CHCl_3$:$CH_3OH$, 95:5) showed no starting material and two new very polar spots. With ice bath cooling, the reaction was quenched using 230 mL $H_2O$, 230 mL 15% NaOH and then 690 mL $H_2O$. After 15 min stirring at room temperature, the mixture was filtered through a d.e. pad, the pad was washed further with small amounts of $CH_2Cl_2$ and the combined organic filtrate was concentrated in vacuo to a yellow oil, 0.287 g. The oil was chromatographed on 10 g silica gel (230–400 mesh) eluting first with $CH_2Cl_2$, then adding increasing percentages of $CH_3OH$. The less polar of the two spots, 2-Fluoro-6-(p-tolyloxy)benzylamine eluted as a yellow oil, 0.120 g.

Mass spectrum (APCl, m/z): 232 (m$^+$), 215 (m$^+$-$NH_3$)

$^1$H-NMR ($CDCl_3$, 400 MHz): d 7.12 (m, 3H), 6.86 (m, 2H), 6.78 (t, 1H), 6.60 (dd, 1H), 3.92 (s, 2H), 2.32 (s, 3H), 1.72 (bs, 2H, $NH_2$).

Further elution of the chromatography provided the more polar component, 2-(p-tolyloxy)benzylamine, as a yellow oil, 0.082 g.

$^1$H-NMR ($CDCl_3$, 400 MHz): d 7.34 (d, 1H), 7.12 (m, 4H), 6.86 (m, 3H), 3.87 (s, 2H), 2.31 (s, 3H), 1.80 (bs, 2H, $NH_2$).

By the same method, the following benzylamino compounds of formula I (where $R^{1-4}$=H) were prepared from the corresponding benzonitriles VI:

| Ex. No. | X | Y | yield (%) | m.p., ° C. (HCl salt) | m/z, m$^+$ | $^1$H-NMR (DMSO-$d_6$, δ) |
|---|---|---|---|---|---|---|
| 2 | H | 3,4-$Cl_2$ | 87 | 198–201 | 270, 268 | (bs, 1H, HCl), 7.65(d, 1H), 7.59(d, 1H), 7.36(m, 2H), 7.22(t, 1H), 7.06(dd, 1H), 6.92(d, 1H), 4.00(s, 2H). |
| 3 | 5-F | 3,4-$Cl_2$ | 67 | 190–194 | 288, 286 | (d, 1H), 7.52(dd, 1H), 7.31 (s, 1H), 7.23(dt, 1H), 7.03 (m, 2H), 3.99(bs, 2H). |

-continued

| Ex. No. | X | Y | yield (%) | m.p., °C. (HCl salt) | m/z, m+ | $^1$H-NMR (DMSO-d$_6$, δ) |
|---|---|---|---|---|---|---|
| 4 | 5-CH$_3$ | 3,4-Cl$_2$ | 54 | 217–219 | 284, 282 | (d, 1H), 7.38(s, 1H), 7.22(d, 1H), 7.20(m, 1H), 6.99(m, 1H), 6.87(d, 1H), 3.94(bs, 2H), 2.28(s, 3H). |
| 5 | 4-OCH$_3$ | 3,4-Cl$_2$ | 37 | 167–168 | 300, 298 | (d, 1H), 7.52(d, 1H), 7.35(d, 1H), 7.06(dd, 1H), 6.82(dd, 1H), 6.45(d, 1H), 3.90(m, 2H), 3.68(s, 3H). |

Example 6

[2-(3,4-Dichlorophenoxy)-5-Trifluoromethylbenzyl]-Dimethylamine Maleate

In a round-bottomed flask fitted with a magnetic stirrer and N$_2$ inlet was placed 0.331 g (4.06 mmol) of dimethylamine hydrochloride (Aldrich) and 0.410 g (4.06 mmol) triethylamine in 25 mL ethanol while stirring until the solution was clear. At room temperature, 1.15 g titanium (IV) isopropoxide (1.2 mL, 4.06 mmol) was added via syringe, followed by 0.680 g (2.03 mmol) of 2-(3,4-dichlorophenoxy)-5-trifluoromethyl-benzaldehyde to give a yellow-brown solution which was stirred overnight. To the resulting cloudy solution was added 0.115 g (3.05 mmol) of sodium borohydride, and stirring was continued for 24 hr. The reaction was then quenched with 6N HCl (~pH=10), stirred another 2 hr and diluted with EtOAc. The aqueous layer was made basic with saturated aqueous Na$_2$CO$_3$, layered with additional EtOAc and the two-layered mixture was filtered through a pad of diatomaceous earth (d.e.), washing the d.e. pad well with EtOAc and H$_2$O. The EtOAc layer was combined with additional extracts of the water layer and the combined organics were washed with saturated aqueous NaCl, dried with MgSO$_4$ and concentrated in vacuo to a yellow oil, 0.626 g.

Mass spectrum: (APCl, m/z) 366, 364 (m+).

$^1$H-NMR (CDCl$_3$, 400 MHz): d 7.78 (s, 1H), 7.47 (dd, 1H), 7.39 (s, 1H), 7.04 (s, 1H), 6.90 (dd, 1H), 6.80 (dd, 1H), 3.48 (s, 2H), 2.26 (s, 6H).

The preceding oil dissolved in anhydrous diethyl ether was treated with 0.199 g of maleic acid in 2 mL of acetone. The mixture was filtered through a thin pad of d.e. to clarify the solution and then was stirred at room temperature for 8 hr. The resulting solids were filtered and washed with Et$_2$O and dried under vacuum, m.p 127–128° C.

Elemental analysis for C$_{16}$H$_{14}$Cl$_2$F$_3$NO.C$_4$H$_4$O$_4$ calculated: C, 50.01; H, 3.77; N, 2.92. Found: C, 49.93; H, 3.85; N, 3.04.

In the same manner the following compounds of formula I were prepared:

| Ex. No. | X | Y | R$^3$ | NR$^1$R$^2$ | mp, °C. | m/z, m+ | Elemental Analysis formula CHN calculated: CHN found |
|---|---|---|---|---|---|---|---|
| 7 | H | 3,4-Cl$_2$ | H | N(CH$_3$)$_2$ | 173–174 | 298, 296 | C$_{15}$H$_{15}$Cl$_2$NO.HCl.H$_2$O C 54.16, H 4.85, N 4.21: C 54.02, H 4.77, N 4.23 |
| 8 | H | 3,4-Cl$_2$ | H | NHCH$_3$ | 126 | 284, 282 | C$_{14}$H$_{13}$Cl$_2$NO.¾C$_4$H$_4$O$_4$ C 54.42, H 4.48, N 3.73: C 54.46, H 4.48, N 3.52 |
| 9 | H | 3,4-Cl$_2$ | H | NHC$_2$H$_5$ | 133–135 | 298, 296 | C$_{15}$H$_{15}$Cl$_2$NO.C$_4$H$_4$O$_4$ C 55.35, H 4.65, N 3.40: C 55.16, H 4.68, N 3.40 |
| 10 | 5-F | 4-Cl | H | NHCH$_3$ | 208–209 | 268, 266 | C$_{14}$H$_{13}$ClFNO.HCl C 55.64, H 4.66, N 4.63: C 55.64, H 4.52, N 4.55 |
| 11 | H | 4-Cl | H | N(CH$_3$)$_2$ | 122 | 264, 262 | C$_{15}$H$_{16}$ClNO.C$_4$H$_4$O$_4$ C 60.40, H 5.33, N 3.70: C 60.46, H 5.29, N 3.71 |
| 12 | H | 4-Cl | H | NHCH$_3$ | 128–129 | 250, 248 | C$_{14}$H$_{14}$ClNO.C$_4$H$_4$O$_4$.⅓H$_2$O C 58.46, H 5.09, N 3.79: C 58.26, H 4.87, N 3.89 |
| 13 | 5-F | 3,4-Cl$_2$ | H | N(CH$_3$)$_2$ | 174–175 | 316, 314 | C$_{15}$H$_{14}$Cl$_2$FNO.HCl C 51.38, H 3.89, N 4.16: C 51.35, H 4.22, N 3.91 |

-continued

| Ex. No. | X | Y | R³ | NR¹R² | mp, °C. | m/z, m⁺ | Elemental Analysis formula CHN calculated: CHN found |
|---|---|---|---|---|---|---|---|
| 14 | 5-F | 3,4-Cl₂ | H | NHCH₃ | 202–203 | 302, 300 | C₁₄H₁₂Cl₂FNO.HCl C 49.95, H 3.89, N 4.16: C 50.05, H 4.04, N 4.21 |
| 15 | 5-F | 3,4-Cl₂ | H | NHCH₃ | 129–130 | 302, 300 | C₁₄H₁₂Cl₂FNO.½C₄H₄O₄ C 50.48, H 4.37, N 3.68: C 50.24, H 4.37, N 3.68 |
| 16 | 5-NO₂ | 3,4-Cl₂ | H | N(CH₃)₂ | | 343, 341 | Not determined |
| 17 | 3-CF₃ | 3,4-Cl₂ | H | N(CH₃)₂ | 229–230 | 366, 364 | C₁₆H₁₄Cl₂F₃NO.HCl.H₂O C 45.90, H 4.09, N 3.35: C 45.70, H 3.82, N 3.30 |
| 18 | H | 3,4-Cl₂ | CH₃ | N(CH₃)₂ | 130–133 | 312, 310 | C₁₆H₁₇Cl₂NO.HCl Not determined |
| 19 | H | 4-CH₃ | H | N(CH₃)₂ | 111–113 | 242 | C₁₆H₁₉NO.C₄H₄O₄.¼H₂O C 66.38, H 6.55, N 3.87: C 66.47, H 6.40, N 3.95 |
| 20 | 4-CF₃ | 3,4-Cl₂ | H | N(CH₃)₂ | 131–133 | 366, 364 | C₁₆H₁₄Cl₂F₃NO.C₄H₄O₄.⅔H₂O C 48.80, H 3.96, N 2.85: C 48.85, H 3.77, N 2.97 |
| 21 | H | 3,4-F₂ | H | N(CH₃)₂ | 145–147 | 264 | C₁₅H₁₅F₂NO.C₄H₄O₄ C 60.15, H 5.05, N 3.69: C 60.09, H 4.91, N 3.74 |
| 22 | H | 3,4-F₂ | H | NHCH₃ | 101–102 | 250 | C₁₄H₁₃F₂NO.C₄H₄O₄ C 59.17, H 4.69, N 3.83: C 59.04, H 4.82, N 3.93 |
| 23 | H | 4-CH₃ | CH₃ | NHCH₃ | 114–116 | 242 | C₁₆H₁₉NO.C₄H₄O₄.⅛H₂O C 66.79, H 6.52, N 3.89: C 66.82, H 6.58, N 3.95 |
| 24 | 6-CF₃ | 3,4-Cl₂ | H | N(CH₃)₂ | 166–168 | 366, 364 | C₁₆H₁₄Cl₂F₃NO.HCl C 47.96, H 3.77, N 3.49: C 47.95, H 3.81, N 3.48 |
| 25 | 6-CF₃ | 3,4-Cl₂ | H | NHCH₃ | 123–125 | 352, 350 | C₁₅H₁₂C₁₂F₃NO.C₄H₄O₄ C 48.94, H 3.45, N 3.00: C 48.90, H 3.58, N 3.23 |
| 26 | 5-F | 3,4-(CH3)₂ | H | NHCH₃ | 123–124 | 260 | C₁₆H₁₈FNO.C₄H₄O₄ C 63 99, H 5.91, N 3.73: C 63.89, H 5.91, N 3.760 |
| 27 | H | 3,4-(CH3)₂ | H | NHCH₃ | 118–119 | 242 | C₁₆H₁₉NO.C₄H₄O₄ C 67.20, H 6.48, N 3.91: C 66.91, H 6.48, N 3.96 |
| 28 | 4-CF₃ | 3,4-Cl₂ | H | NHCH₃ | 164–166 | 352, 350 | C₁₅H₁₂Cl₂F₃NO.C₄H₄O₄ C 48.94, H 3.46, N 3.00: C 49.02, H 3.22, N 3.06 |
| 29 | 4-Cl | 3,4-Cl₂ | H | NHCH₃ | 132–133 | 318, 316 | C₁₄H₁₂Cl₃NO.C₄H₄O₄ C 49.96, H 3.72, N 3.24: C 49.89, H 3.49, N 3.25 |
| 30 | 5-F | 3,4-(OCH₂O) | H | NHCH₃ | 96–97 | 276 | C₁₅H₁₄NO₃.C₄H₄O₄ C 58.31, H 4.63, N 3.57: C 58.34, H 4.38, N 3.62 |
| 31 | 3-F | 3,4-Cl₂ | H | NHCH₃ | 138–140 | 302, 300 | C₁₄H₁₂Cl₂FNO.C₄H₄O₄ C 51.94, H 3.87, N 3.36: C |

-continued

| Ex. No. | X | Y | R³ | NR¹R² | mp, ° C. | m/z, m⁺ | Elemental Analysis formula CHN calculated: CHN found |
|---|---|---|---|---|---|---|---|
| 32 | 5-F | 3,4-Cl₂ | CH₃ | NHCH₃ | 127 | 316, 314 | 51.96, H 3.87, N 3.44<br>$C_{15}H_{14}Cl_2FNO \cdot C_4H_4O_4$<br>C 53.04, H 4.22, N 3.25: C 53.23, H 4.21, N 3.23 |
| 33 | 5-F | 4-Cl | CH₃ | NHCH₃ | 173–175 | 282, 280 | $C_{15}H_{15}ClFNO \cdot HCl$<br>C 56.98, H 5.10, N 4.43: C 56.90, H 5.34, N 4.42 |
| 34 | 4-F | 3,4-Cl₂ | H | NHCH₃ | 151–152 | | $C_{14}H_{12}Cl_2FNO \cdot C_4H_4O_4$<br>C 50.31, H 4.10, N 3.26: C 50.28, H 3.93, N 3.24 |
| 35 | 5-OCH₃ | 3,4-Cl₂ | H | NHCH₃ | 140–141 | 314, 312 | $C_{15}H_{15}Cl_2NO_2 \cdot HCl \cdot \frac{1}{4}H_2O$<br>C 51.01, H 4.71, N 3.97: C 51.08, H 4.54, N 3.91 |
| 36 | H | 4-Cl | CH3 | NHCH₃ | 147–149 | 264, 262 | $C_{15}H_{16}ClNO \cdot HCl$<br>C 60.41, H 5.74, N 4.69: C 60.02, H 5.74, N 4.65 |
| 37 | 5-F | 4-Cl | H | N(CH₃)₂ | 103 | 282, 280 | $C_{15}H_{15}ClFNO \cdot C_4H_4O_4$<br>C 57.65, H 4.83, N 3.53: C 57.74, H 4.82, N 3.47 |
| 38 | 4,5-(OCH3)₂ | 3,4-Cl₂ | H | NHCH₃ | 143–145 | 344, 342 | $C_{16}H_{17}Cl_2NO_3 \cdot HCl$<br>C 47.37, H 5.20, N 3.45: C 47.36, H 4.93, N 3.49 |
| 39 | 4,5-(CH3)₂ | 3,4-Cl₂ | H | NHCH₃ | | 312, 310 | $C_{16}H_{17}Cl_2NO \cdot HCl$<br>C 55.43, H 5.23, N 4.04: C 55.84, H 4.80, N 3.80 |
| 40 | 5-Br | 3,4-Cl₂ | H | NHCH₃ | 206–210 | 364, 362 | $C_{14}H_{12}BrCl_2NO \cdot HCl$<br>C 42.30, H 3.30, N 3.52: C 42.13, H 3.13, N 3.36 |
| 41 | 4-Br | 3,4-Cl₂ | H | NHCH₃ | 185–189 | 364, 362 | $C_{14}H_{12}BrCl_2NO \cdot HCl$<br>C 42.30, H 3.30, N 3.52: C 42.03, H 3.07, N 3.33 |
| 42 | H | 4-SCH₃ | H | N(CH₃)₂ | 171–173 | 274 | $C_{16}H_{19}NOS \cdot HCl$<br>Not determined |
| 43 | H | 3,4-Cl₂ | H | NHCH₃ | 162–164 | 298, 296 | $C_{15}H_{15}Cl_2NO \cdot HCl$<br>C 54.32, H 4.55, N 4.22. C 54.05, H 4.76, N 4.17 |
| 44 | 4-CN | 3,4-Cl₂ | H | NHCH₃ | 200–205 | 309, 307 | $C_{15}H_{12}Cl_2N_2O \cdot HCl \cdot \frac{1}{4}H_2O$<br>C 51.75, H 3.91, N 8.05: C 51.82, H 3.80, N 7.83 |
| 45 | 5-SO₂-NHCH₃ | 3,4-Cl₂ | H | NHCH₃ | 202–204 | 376, 374 | $C_{15}H_{16}Cl_2N_2O_3S \cdot HCl$<br>C 43.75, H 4.16, N 6.80: C 43.66, H 3.88, N 6.37 |
| 46 | 4-OCH₃ | 3,4-Cl₂ | H | N(CH₃)2 | 113–115 | 328, 326 | $C_{16}H_{17}Cl_2NO_2 \cdot C_4H_4O_4$<br>C 54.31, H 4.78, N 3.17: C 54.34, H 4.59, N 2.97 |
| 47 | 5-CH₃ | 3,4-Cl₂ | H | N(CH₃)2 | 196–198 | 312, 310 | $C_{16}H_{17}Cl_2N \cdot HCl$<br>C 55.43, H 5.23, N 4.04: C 55.28, H 5.12, N 4.00 |

Example 52

(2-Fluoro-6-(P-Tolyloxy)Benzyl)-Dimethylamine Maleate (I, $R^{1,2}$=$CH_3$)

Under $N_2$, a solution of 0.120 g (0.52 mmol) of 2-fluoro-6-(p-tolyloxy)benzylamine from example 3) in 2 mL of $CH_3OH$ was treated with 215 mL (2.86 mmol) of 37% aqueous formaldehyde (Aldrich), producing a solid precipitate. Sodium triacetoxyborohydride (0.319 g, 1.43 mmol) was then added, producing some foaming before becoming a clear solution. After stirring at room temperature overnight, $H_2O$ and EtOAc were added, the aqueous layer was further extracted with EtOAc, and the organic layers were combined and washed with $H_2O$ and saturated NaCl. After drying over $MgSO_4$, the solvent was removed in vacuo to give a light yellow film, 0.110 g.

Mass spectrum (APCl, m/z): 260 ($m^{+1}$).

$^1$H-NMR ($CDCl_3$, 400 MHz): d 7.28 (m, 1H), 7.14 (m, 2H), 6.91 (m, 2H), 6.83(t, 1H), 6.56 (d, 1H), 4.38 (s, 2H), 2.79 (s, 6H), 2.32 (s, 3H).

The crude amine (84 mg) was dissolved in $Et_2O$ and treated with 38 mg (1 equiv.) of maleic acid in 2 mL of acetone. After stirring at room temperature for 18 hr, the white solid salt was filtered and washed with small amounts of $Et_2O$ and dried under high vacuum to give 0.048 g of the title product, m.p. 147–148° C.

Elemental analysis for $C_{16}H_{18}FNO.C_4H_4O_4$ calculated: C, 63.99; H, 5.90; N, 3.73. Found: C, 63.97; H, 5.91; N, 3.67.

Example 53

4-(3,4-Dichlorophenoxy)-3-(Dimethylaminomethyl)-Phenylamine Hydrochloride

Under $N_2$, in a 250 mL Parr apparatus bottle, 0.265 9 of 10% Pd on carbon was treated with 30 mL of EtOAc and 0.53 g (1.55 mmol) of [2-(3,4-dichlorophenoxy)-5-nitrobenzyl]-dimethylamine (prepared as in Preparation 1) followed by 2 drops of acetic acid. The mixture was hydrogenated at 40–45 psi of $H_2$ for 90 min, at which time no starting material was visible by tlc (90:10 $CHCl_3$:$CH_3OH$). Saturated $NaHCO_3$ was added to adjust the pH>7 and the solution was filtered through a pad of d.e., washing the pad with $H_2O$ and EtOAc. The organic layers were combined, washed with $H_2O$ and saturated NaCl, dried over $MgSO_4$ and concentrated in vacuo to a tan oil, 0.325 g.

Mass spectrum (APCl, m/z): 313, 311.

$^1$H-NMR ($CDCl_3$, 400 MHz): d 7.39 (m, 2H), 7.21 (m, 3H), 6.70 (dd, 1H), 4.52 (s, 2H), 2.89 (s, 6H).

The oil was dissolved in $Et_2O$ and treated with 2.1 mL of 1.0 M HCl in $Et_2O$ (Aldrich), stirred at room temperature for 2 hr. and filtered. After drying in vacuo, the title product weighed 0.286 g, m.p. 228° C.

Example 54

N-[4(3,4-Dichlorophenoxy)-3-Dimethylaminomethylphenyl]-Acetamide Hydrochloride To a suspension of 0.130 g (0.375 mmol) of 4-(3,4-dichlorophenoxy)-3-(dimethylaminomethyl)-phenylamine hydrochloride (from example 53) in 3 mL of toluene at room temperature, under $N_2$, was added 110 mL of triethylamine. After 2 hr, 28 mL (0.394 mmol) of acetyl chloride was added and the mixture was stirred another 1 hr before being diluted with EtOAc and saturated aqueous $NaHCO_3$. The aqueous layer was further extracted with EtOAc and the organic layers were combined, washed with $H_2O$ and saturated NaCl, dried with $MgSO_4$ and concentrated to a tan oil, 0.116 g.

Mass spectrum (APCl, m/z): 355, 353.

The crude product was dissolved in $Et_2O$ and treated with 330 mL of 1.0 M HCl in $Et_2O$. After stirring at room temperature, the solids were filtered and washed with small amounts of $Et_2O$, then dried in vacuo to give the title product, 88 mg, m.p. 199–202° C.

Elemental Analysis calculated for $C_{17}H_{18}Cl_2N_2O_2$.HCl.¾ $H_2O$: C, 50.64; H, 5.12; N, 6.95. Found: C, 50.51; H, 5.19; N, 6.66.

Example 55

2-[2-(3,4-Dichlorophenoxy)-5-Fluorophenyl]-Pyrrolidine Hydrochloride

A. 2-(3,4-Dichlorophenoxy)-5-Fluoro-Benzoic Acid

Under $N_2$ in a round-bottomed flask fitted with a reflux condenser and magnetic stirrer were placed 6.37 g (19.55 mmol) of cesium carbonate and 3.2 g (19.55 mmol) of 3,4-dichlorophenol (both from Aldrich Chem. Co., Milwaukee, Wis.) in 60 mL of anhydrous toluene. After stirring the mixture for 5 min., 89 mg (0.24 mmol) of copper (II) trifluoromethansulfonate (copper triflate) and 0.26 g (9.78 mmol) of 5-fluoro-2-iodobenzoic acid (prepared according to the method in Collection of Czechoslovakian Chemical Communications, 1975, vol. 40, p728) were added and the mixture was heated to reflux overnight. Progress of the reaction was monitored using thin layer chromatography (tlc), eluting with $CHCl_3$:$CH_3OH$:AcOH (9:1:0.5). After allowing the reaction to cool to room temperature, the mixture was diluted with water and EtOAc; the aqueous layer was acidified with 6 N HCl and re-extracted with additional EtOAc. The organic layers were combined, washed with $H_2O$ and saturated NaCl and dried over $MgSO_4$. Removal of the solvent in vacuo gave a dark brown colored oil, 2.6 g, as a mixture of title product and unreacted 5-fluoro-2-iodobenzoic acid.

Alternatively, a solution of 4.28 g (15 mmol) of 2-(3,4-dichloro-phenoxy)-5-fluorobenzaldehyde (Preparation no. 5) in 25 mL of acetone was cooled to 5–10° C. and treated via syringe with 5.8 mL (15.6 mmol) of 2.67 M Jones reagent*. After 1 hr at this temperature, the reaction was quenched with 8 mL of isopropanol, allowed to warm to 25° C., and filtered through a pad of d.e. The filtrate was concentrated in vacuo to approximately ¼ volume, diluted with water and extracted several times with $CHCl_3$. The organic layers were washed with water, then with saturated NaCl and finally dried over $MgSO_4$ and concentrated to provide 2-(3,4-dichlorophenoxy)-5-fluoro-benzoic acid as a tan solid, 4.19 g. $^1$H-nmr ($CDCl_3$, 400 MHz, δ): 7.78 (dd, 1H), 7.38 (d, 1H), 7.27 (m, 1H), 6.98 (m, 2H), 6.81 (dd, 1H).

*Jones reagent was prepared from 13.4 g of chromium trioxide and 11.5 mL of concentrated $H_2SO_4$, diluted to a final volume of 50 mL with $H_2O$.

B. 2-(3,4-Dichlorophenoxy)-5-Fluoro-Benzoic Acid Ethyl Ester

The preceding mixture in 75 mL of ethanol was treated with 1 mL of $H_2SO_4$ and heated to reflux for 7 hr, then stirred overnight at room temperature. The solvent was removed in vacuo and the residue was dissolved in EtOAc, was with water, saturated aqueous $Na_2CO_3$ and then water. After drying with $MgSO_4$, the solvent was evaporated to give a brown oil, 2.1 g. $^1$H-nmr ($CDCl_3$, 400 MHz, δ): 7.64 (dd, 1H), 7.31 (d, 1H), 7.22 (m, 1H), 7.03 (dd, 1H), 6.92 (s, 1H), 6.72 (dd, 1H), 4.24 (q, 2H), 1.19 (t, 3H).

C. 3-[2-(3,4-Dichlorophenoxy)-5-Fluorobenzoyl]-1-Vinyl-Pyrrolidin-2-One

Under $N_2$, a solution of 12.2 mL (12.2 mmol) of 1.0M lithium bis-(trimethylsilyl)amide in THF (Aldrich Chem. Co.) was stirred and cooled to −30° C. while 781 μL (0.812 g, 7.31 mmol) of 1-vinyl-2-pyrrolidinone (Aldrich Chem. Co.) was added via syringe. After stirring at this temperature for 1 hr, the preceding ethyl ester in 20 mL of THF was added to produce a nearly black solution. This mixture was stirred at room temperature for 72 hr, then diluted with water and EtOAc. The aqueous layer was further extracted with EtOAc and the organic layers were combined, washed with water and saturated NaCl, dried over $MgSO_4$ and concentrated in vacuo to a tan foam, 2.18 g. This material was used without purification in the following step.

D. 5-[2-(3,4-Dichlorophenoxy)-5-Fluorophenyl]-2,3-Dihydro-1H-Pyrrole

The preceding material was combined with 40 mL of 6N HCl and refluxed for 30 min., producing a gummy precipitate. 1,4-Dioxane (30 mL) was added and the resulting solution was refluxed an additional 30 hr to give a black solution. The reaction was made basic with saturated aqueous $K_2CO_3$ and extracted three times with EtOAc. The combined organic extracts were washed with water and saturated NaCl, dried with $MgSO_4$ and treated with activated charcoal (Darco G60). Filtration through d.e., washing the pad well with EtOAc and concentration of the filtrate provided a tan oil, 0.803 g, used without further purification in the next step. Mass spectrum (m/e): 325, 323 (m$^+$).

E. 2-[2-(3,4-Dichlorophenoxy)-5-Fluorophenyl]-Pyrrolidine Hydro-Chloride

To 0.300 g (0.93 mmol) of the preceding material in 15 mL of absolute ethanol was added 70 mg (1.86 mmol) of sodium borohydride at room temperature under an $N_2$ atmosphere (Caution: foaming). After 24 hr, a tlc (CHCl$_3$:CH$_3$OH, 95:5) showed a new polar product had formed. Water was added to quench residual sodium borohydride and the mixture was evaporated to a clear oil which was redissolved in EtOAc and washed with water. The organic layer was further washed with water, saturated NaCl and then dried with $MgSO_4$. Removal of the solvent in vacuo gave a clear film, 0.202 g.

Mass Spectrum (m/e): 328, 326 (m$^{+1}$).

$^1$H-nmr (CDCl$_3$, 400 MHz, δ): 7.35 (dd, 1H), 7.32 (d, 1H), 6.96 (d, 1H), 6.87 (m, 2H), 6.73 (dd, 1H), 4.26 (t, 1H), 3.11 (m, 1H), 2.97 (m, 1H), 1.78 (m, 2H), 1.52 (m, 1H).

The free base was dissolved in 5 mL Et$_2$O and treated with 622 mL of 1.0 M HCl in Et$_2$O, then stirred for 1.5 hr to produce the title compound hydrochloride salt as pale yellow solids, 165 mg, m.p. 171–173° C.

Mass Spectrum (m/e): 328, 326 (m$^{+1}$).

Elemental analysis calculated for C$_{16}$H$_{14}$Cl$_2$FNO.HCl: C, 52.99; H, 4.17; N, 3.86. Found: C, 53.23; H, 4.25; N, 3.89.

Example 56

[2-(3,4-Dichlorophenoxy)-5-Fluorobenzyl]-Methylamine

Under $N_2$, a mixture of 0.313 g (1.0 mmol) of 2-(3,4-dichlorophenoxy)-5-fluoro-N-methyl-benzamide in 5.0 mL of anhydrous tetrahydrofuran (THF) was treated via syringe with 4.0 mL (4.0 mmol) of 1.0 M BH$_3$ in THF (Aldrich Chem. Co.). and the mixture was heated to reflux for a total of 48 hr. The reaction was quenched by the addition of 25 mL of 6N HCl and heating to reflux until the free amine could be detected by tlc (CHCl$_3$:CH$_3$OH:TEA, (95:5:1)). The cooled mixture was then diluted with water, basified with K$_2$CO$_3$ and extracted with EtOAc. The combined organic layers were washed with water and saturated NaCl, then dried with MgSO$_4$, filtered and concentrated in vacuo to the free base as a light brown oil, 0.164 g, 54%). This compound was converted to the hydrochloride salt as described previously, m.p. 200–202°.

Example 57

2-(3,4-Dichlorophenoxy)-5-Fluoro-Benzylamine

A flame-dried flask containing $N_2$ inlet and magnetic stirrer was charged with 3.0 mL of 2.0 M borane methyl sulfide complex in THF (6.0 mmol, Aldrich Chem. Co.), followed by an additional 10 mL of anhydrous THF at room temperature. While stirring, 0.562 g (2.0 mmol) of 2-(3,4-dichlorophenoxy)-5-fluoro-benzonitrile (title compound of Preparation 37) was added slowly via syringe, causing some mild foaming. After the addition, the reaction was heated at reflux for a total of 3 hr, and a tlc (CHCl$_3$:CH$_3$OH:conc. NH$_4$OH, 95:5:1) showed no starting material remaining. With ice bath cooling, the reaction was quenched using 10 mL of 6N HCl, heated to reflux an additional 1 hr to break the boron complex and slowly made basic with saturated aqueous Na$_2$CO$_3$. The mixture was diluted with water and EtOAc, the organic layer was combined with a second EtOAc extraction of the aqueous layer and then washed with water and saturated aqueous NaCl. After drying over MgSO4, the solvent was removed in vacuo to give a yellow tan oil, 0.676 g. The oil was partitioned between Et$_2$O and 6N HCl, the Et$_2$O layer was reextracted with 6N HCl and the aqueous layers were combined, made basic with aqueous Na$_2$CO$_3$ and reextracted with Et$_2$O. These latter organic extracts were dried (MgSO$_4$) and concentrated in vacuo to a tan oil, 0.538 g.

Mass spectrum (APCl, m/z): 286 (m$^+$), 288.

The oil was dissolved in Et$_2$O and treated with 2.0 mL of 1.0 M HCl in Et$_2$O. The resulting solids were stirred at room temperature for 2 hr, filtered, washed with Et$_2$O and dried under vacuum to give the hydrochloride salt of the title product, 0.434 g, m.p. 190–194° C.

Elemental Analysis calculated for C$_{13}$H$_{10}$Cl$_2$FNO.HCl: C, 48.40; H, 3.43; N, 4.34. Found: C, 48.22; H, 3.80; N, 4.28.

What is claimed is:

1. A compound of the formula

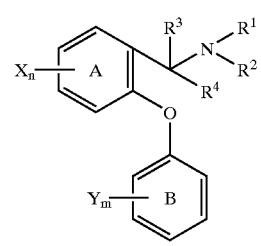

I wherein phenyl ring A and phenyl ring B can each, independently, be replaced by a naphthyl group, and wherein when phenyl ring A is replaced by a naphthyl group, the ethereal oxygen of structure I and the carbon to which R$^3$, R$^4$ and NR$^1$R$^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl;

$R^3$ and $R^4$ are selected, independently, from hydrogen and $(C_1-C_4)$alkyl optionally substituted with from one to three fluorine atoms, or $R^3$ and $R^4$ together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

each X is selected, independently, from hydrogen, chloro, fluoro, bromo or Iodo, $(C_1-C_4)$alkyl optionally substituted with from one to three fluorine atoms, $(C_1-C_4)$ alkoxy optionally substituted with from one to three fluorine atoms, cyano, nitro, amino, $(C_1-C_4)$ alkylamino, di-$[(C_1-C_4)$alkyl]amino, $NR^5(C=O)$ $(C_1-C_4)$alkyl, $SO_2NR^5R^6$ and $SO_p(C_1-C_8)$alkyl, wherein $R^5$ and $R^6$ are selected, independently, from hydrogen and $(C_1-C_6)$alkyl, and p is zero, one or two; and each Y is selected, independently, from hydrogen, $(C_1-C_6)$alkyl and halo;

with the proviso that; at least one X must be other than hydrogen when (i) $R^3$ and $R^4$ are both hydrogen, (ii) $R^1$ and $R^2$ are selected, independently, from hydrogen and $(C_1-C_4)$alkyl, and (iii) ring B is mono- or disubstituted with, respectively, one or two halo groups;

or a pharmaceutically acceptable salt thereof.

2. A compound or salt according to claim 1, wherein n is one, X is fluoro, $R^3$ and $R^4$ are hydrogen, $R^1$ is hydrogen, $R^2$ is methyl, m is two and Y is $Y_m$ is 3,4-dichloro.

3. A compound or salt according to claim 1, wherein m is zero, n is one, $R^3$ and $R^4$ are hydrogen, X is chloro, bromo, Iodo or methyl, $R^1$ is hydrogen and $R^2$ is methyl.

4. A compound or salt according to claim 1, wherein said compound or salt is selected from the following compounds and their pharmaceutically acceptable salts:

[2-(3,4-Dichlorophenoxy)-5-fluorobenzyl]-dimethylamine;

[2-(3,4-Dichlorophenoxy)-5-fluorobenzyl]-methylamine;

[2-(3,4-Dichlorophenoxy)-5-trifluoromethylbenzyl]-dimethylamine;

N-[4-(3,4-Dichlorophenoxy)-3-dimethylaminomethyl-phenyl]-acetamide;

{1-[2-(3,4-Dichlorophenoxy)phenyl]-ethyl}-dimethylamine;

[2-(3,4-Dichlorophenoxy)-4-trifluoromethylbenzyl]-dimethylamine;

[2-(3,4-Dichlorophenoxy)-4-trifluoromethylbenzyl]-methylamine;

[4-Chloro-2-(3,4-dichlorophenoxy)-benzyl]-methylamine;

{1-[2-(3,4-Dichlorophenoxy)-5-fluorophenyl]-ethyl}-methylamine;

{1-[2-(3,4-Dichlorophenoxy)phenyl]-ethyl}-methylamine;

{1-[2-(4-Chlorophenoxy)phenyl]ethyl}-methylamine;

[2-(3,4-Dichlorophenoxy)-5-methoxybenzyl]-methylamine;

[2-(4-Chlorophenoxy)-5-fluorobenzyl]-methylamine;

{1-[2-(4-Chlorophenoxy)-5-fluorophenyl]-ethyl}-methylamine;

[2-(3,4-Dichlorophenoxy)-5-methylbenzyl]-dimethylamine;

[4-Bromo-2-(3,4-dichlorophenoxy)-benzyl]-methylamine;

[5-Bromo-2-(3,4-dichlorophenoxy)-benzyl]-methylamine;

[2-(3,4-Dichlorophenoxy)-4,5-dimethoxybenzyl]-methylamine;

[2-(3,4-Dichlorophenoxy)-4-methoxybenzyl]-dimethylamine;

4-(3,4-Dichlorophenoxy)-3-methylaminomethyl-benzonitrile;

[2-(3,4-Dichlorophenoxy)-4,5-dimethylbenzyl]-methylamine;

3-(3,4-Dichlorphenoxy)-4-methylaminomethyl-benzonitrile;

(+)-{1-[2-(3,4-Dichlorophenoxy)-5-fluorophenyl]-ethyl}-methylamine;

(−)-{1-[2-(3,4-Dichlorophenoxy)-5-fluorophenyl]-ethyl}-methylamine;

[2-(3,4-Dichlorophenoxy)-5-trifluoromethyl-benzyl]-methylamine;

[2-(3,4-Dichlorophenoxy)-4-methoxybenzyl]-methylamine;

[2-(4-Chloro-3-fluorophenoxy)-5-fluorobenzyl]-methylamine;

[2-(3-Chloro-4-fluorophenoxy)-5-fluorobenzyl]-methylamine.

5. A pharmaceutical composition for treating a disorder or condition selected from hypertension, depression, depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression, generalized anxiety disorder, phobias, agoraphobia, social phobia and simple phobias, posttraumatic stress syndrome, avoidant personality disorder, premature ejaculation, eating disorders, anorexia nervosa and bulimia nervosa, obesity, chemical dependencies, addictions to alcohol, cocaine, heroin, phenobarbital, nicotine and benzodiazepines, cluster headache, migraine, pain, Alzheimer's disease, obsessive-compulsive disorder, panic disorder, memory disorders, dementia, amnestic disorders, and age-related cognitive decline, Parkinson's diseases, dementia in Parkinson's disease, neuroleptic-induced parkinsonism and tardive dyskinesias, endocrine disorders, hyperprolactinaemia, vasospasm in the cerebral vasculature, cerebellar ataxia, gastrointestinal tract disorders involving changes in motility and secretion, negative symptoms of schizophrenia, premenstrual syndrome, fibromyalgia syndrome, stress incontinence, Tourette's syndrome, trichotillomania, kleptomania, male impotence, attention deficit hyperactivity disorder, chronic paroxysmal hemicrania and headache associated with vascular disorders in a mammal, comprising an amount of a compound according to claim 1 that is effective in treating such disorder or condition and a pharmaceutically acceptable carrier.

6. A pharmaceutical composition for treating a disorder or condition that can be treated by inhibiting the reuptake of serotonin, dopamine or norepinephrine in a mammal, comprising an amount of a compound according to claim 1, that is effective in treating such disorder or condition and a pharmaceutically acceptable carrier.

7. A method for treating a disorder or condition selected from hypertension, depression, depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression, generalized anxiety disorder, phobias, agoraphobia, social phobia and simple phobias, posttraumatic stress syndrome, avoidant personality disorder, premature ejaculation, eating disorders, anorexia nervosa and bulimia nervosa, obesity, chemical dependencies, addictions to alcohol, cocaine, heroin, phenobarbital, nicotine and benzodiazepines, cluster headache, migraine, pain, Alzheimer's disease, obsessive-compulsive disorder, panic disorder, memory disorders, dementia, amnestic disorders, and age-related cognitive decline, Parkinson's diseases, dementia in Parkinson's disease, neuroleptic-induced parkinsonism and tardive dyskinesias, endocrine disorders, hyperprolactinaemia, vasospasm in the cerebral vasculature, cerebellar ataxia, gastrointestinal tract disorders involving changes in motility and secretion, negative symptoms of schizophrenia, premenstrual syndrome, fibromyalgia syndrome, stress incontinence, Tourette's syndrome, trichotillomania, kleptomania, male impotence, attention deficit hyperactivity disorder, chronic paroxysmal hemicrania and headache associated with vascular disorders in a mammal, comprising a serotonin, dopamine or norepinephrine reuptake inhibiting effective amount of a compound of the formula I, or a pharmaceutically acceptable salt thereof, and a pharmaceutically acceptable carrier.

8. A pharmaceutical composition for treating a disorder or condition that can be treated by inhibiting the reuptake of serotonin, norepinephrine or dopamine in a mammal, comprising serotonin, dopamine or norepinephrine reuptake inhibiting effective amount of a compound according to claim 1, and a pharmaceutically acceptable carrier.

* * * * *